(12) United States Patent
Yang et al.

(10) Patent No.: US 11,976,285 B2
(45) Date of Patent: May 7, 2024

(54) MAIZE GENE *KRN2* AND USES THEREOF

(71) Applicant: CHINA AGRICULTURAL UNIVERSITY, Beijing (CN)

(72) Inventors: Xiaohong Yang, Beijing (CN); Jiansheng Li, Beijing (CN); Wenkang Chen, Beijing (CN); Xuan Zhang, Beijing (CN); Lichun Cai, Beijing (CN); Yirong Zhang, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 16/767,207

(22) PCT Filed: Nov. 28, 2018

(86) PCT No.: PCT/CN2018/117844
§ 371 (c)(1),
(2) Date: May 27, 2020

(87) PCT Pub. No.: WO2019/105366
PCT Pub. Date: Jun. 6, 2019

(65) Prior Publication Data
US 2021/0079410 A1 Mar. 18, 2021

(30) Foreign Application Priority Data
Nov. 28, 2017 (CN) .......................... 201711217216.3

(51) Int. Cl.
*C12N 15/82* (2006.01)
*C07K 14/415* (2006.01)
*C12Q 1/6895* (2018.01)

(52) U.S. Cl.
CPC ..... *C12N 15/8218* (2013.01); *C12N 15/8261* (2013.01); *C07K 14/415* (2013.01); *C12N 15/8213* (2013.01); *C12Q 1/6895* (2013.01); *C12Q 2600/13* (2013.01); *C12Q 2600/156* (2013.01); *C12Q 2600/158* (2013.01)

(58) Field of Classification Search
CPC ........................ C12N 15/8218; C12Q 2600/13
See application file for complete search history.

(56) References Cited

U.S. PATENT DOCUMENTS

2006/0141495 A1 6/2006 Wu
2010/0313299 A1* 12/2010 Sanz Molinero .... C07K 14/415
800/278
2017/0114356 A1 4/2017 Li et al.

FOREIGN PATENT DOCUMENTS

| CN | 103687950 A | 3/2014 |
|---|---|---|
| CN | 103951741 A | 7/2014 |
| CN | 107354215 A | 11/2017 |
| WO | 2009/068564 A1 | 6/2009 |
| WO | 2009/091518 A2 | 7/2009 |
| WO | 2014/106838 A2 | 7/2014 |

OTHER PUBLICATIONS

Studer et al (OEL26113, published Sep. 2016) (Year: 2016).*
Su et al (High Density Linkage Map Construction and Mapping of Yield Trait QTLs in Maize (*Zea mays*) Using the Genotyping-by-Sequencing (GBS) Technology. Frontiers in Plant Science. 1-14, 2017) (Year: 2017).*
Li et al (Combined Linkage and Association Mapping Reveals QTL and Candidate Genes for Plant and Ear Height in Maize. Frontiers in Plant Science. 1-11, 2016) (Year: 2016).*
Ge et al (Minimal-length short hairpin RNAs: The relationship of structure and RNAi activity. RNA, 16:106-117, 2010) (Year: 2010).*
Hall (Unravelling the general properties of siRNAs: strength in numbers and lessons from the past. Nature Reviews. Genetics 5:552-557, 2004) (Year: 2004).*
Ali et al (Seed Composition and Seed Oil Antioxidant Activity of Maize Under Water Stress. J Am Oil Chem Soc. 87:1179-1187, 2010). (Year: 2010).*
Sequence Matched (published 2016) (Year: 2016).*
Muhammad et al (RNA Interference: A Natural Immune System of Plants to Counteract Biotic Stressors. Cells. 1-29, 2019). (Year: 2019).*
Ali et al. (Seed Composition and Seed Oil Antioxidant Activity of Maize Under Water Stress. J Am Oil Chem Soc. 87: 1-9, 2010). (Year: 2010).*
Muhammad, Tayeb, et al. "RNA interference: a natural immune system of plants to counteract biotic stressors." Cells 8.1 (2019): 38. (Year: 2019).*
GenBank Accesson No. ONM14875, Transducin/WD40 repeat-like superfamily protein [*Zea mays*]. 2 pages, Feb. 6, 2017.
Sekhon et al., Genome-wide atlas of transcription during maize development. Plant J. 2011;66(4):553-563.
Su et al., High Density Linkage Map Construction and Mapping of Yield Trait QTLs in Maize (*Zea mays*) Using the Genotyping-by-Sequencing (GBS) Technology. Front Plant Sci. 2017;8:706, 14 pages.
Sun, Bioinformatics Analysis of the Gene GRMZM2G398848 Related to Kernal Row Number in Maize. Heilongjiang Agricultural Sciences. Dec. 31, 2016;11:4-7.
Wang, Combining Large Recombinant Inbred Lines Population and Ultra-high Density Molecular Markers to Identify QTL for Important Agronomic Traits in Maize. Chinese Doctoral Dissertation Full Text Database, Thesis. 93 pages, Nov. 2014.
International Search Report for Application No. PCT/CN2018/117844, dated Feb. 27, 2019, 5 pages.
NCBI Reference No. XP_008669015.1. WD repeat-containing protein 44 [*Zea mays*]. 2 pages, Aug. 31, 2020.

* cited by examiner

*Primary Examiner* — Charles Logsdon
*Assistant Examiner* — Wayne Zhong
(74) *Attorney, Agent, or Firm* — McCarter & English, LLP; Wei Song; Miao Yu

(57) ABSTRACT

Provided herein are KRN2 gene controlling kernel row number in plant, molecular markers closely linked to KRN2 and their application in molecular breeding.

18 Claims, 12 Drawing Sheets

Figure 1:
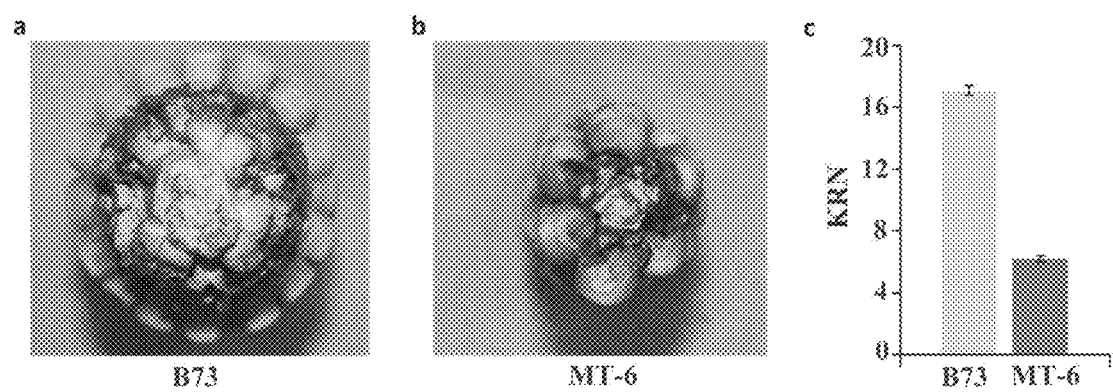

Specification includes a Sequence Listing.

SEQUENCE LISTING

<160> NUMBER OF SEQ ID NOS: 25

<210> SEQ ID NO 1
<211> LENGTH: 696
<212> TYPE: PRT
<213> ORGANISM: Maize

<400> SEQUENCE: 1

```
Met Glu Gly Cys Gln Leu Leu Val Gly Cys Arg Met Glu Met Glu Glu
1               5                   10                  15

Glu Ala Phe Phe Asp Ser Arg Glu Glu Leu Thr Ala Ser Pro Ala Pro
            20                  25                  30

Ser Pro Gly Pro Ala Leu Pro Trp Ser Gly Ser Leu Asp Ser Val Cys
        35                  40                  45

Gln Arg Arg Glu Arg Phe Met Arg Ser Met Gly Leu Glu Cys Cys Pro
    50                  55                  60

Ala Pro Leu Gln Ala Asp Ala Val Ala Thr Val Gly Asp Val Asp Lys
65                  70                  75                  80

Glu Glu Glu Ala Val Pro Glu Phe Gly Arg Ser Trp Ser Gln Ser Asp
                85                  90                  95

Glu Asn Asp Cys Ser Met Ser Ser Trp Ser Thr Glu Glu Thr Lys Ser
            100                 105                 110

Leu Glu Asp Gly Val Ser Asp Asp Asn Ser Val Ser Gly Ser Ser Arg
        115                 120                 125

Asp Asp Ala Ser Ser Lys Val Ser Arg Ser Phe Ser Ser Leu Ser Phe
    130                 135                 140

Ile Gln Arg Leu Met Ser Arg Ser Gly Lys Leu Ser Gly Val Pro Lys
145                 150                 155                 160

Ala Val Glu Arg Arg Asn Gly Trp Leu Arg Arg Leu Gly Leu Arg
                165                 170                 175

Ser Gly Ile Leu Asp His Gly Gly Asp Glu Ala Ser Thr Ser Ser Ser
            180                 185                 190

Glu Ser Glu Gln Asn Arg Gly Gly Arg Tyr Glu Arg Val Lys Val Arg
        195                 200                 205

Ser Tyr Arg Lys Arg Ser Lys Glu Leu Ser Ala Val Tyr Gln Gly Gln
    210                 215                 220

Val Ile Lys Gly His Asp Gly Ala Ile Leu Ala Met Lys Phe Ser Pro
225                 230                 235                 240

Asp Gly Gln Phe Leu Ala Thr Gly Gly Glu Asp Gly Val Val Arg Val
                245                 250                 255

Trp Gly Val Ala Gln Ser Glu Asp Cys Lys Ile Pro Met Asp Asp Pro
            260                 265                 270
```

-continued

```
Ser Cys Val Tyr Leu Lys Ala His Arg Gln Ser Gly Leu Gly Pro Val
            275                 280                 285
Asp Ala Asp Asn Glu Lys Lys Cys Lys Val Lys Gly Val Lys Gln Ser
290                 295                 300
Ala Asp Ser Ala Cys Val Val Ile Pro Thr Val Val Phe Gln Ile Ser
305                 310                 315                 320
Lys Gln Pro Leu His Glu Phe Arg Gly His Ser Gly Asp Val Leu Ser
                325                 330                 335
Leu Ser Trp Ser Asn Asn Lys His Leu Ser Ala Ser Thr Asp Lys
            340                 345                 350
Ser Val Arg Leu Trp Glu Ile Gly Ser Ala Asn Cys Ile Thr Val Phe
            355                 360                 365
Pro His Ser Asn Phe Val Thr Cys Val Gln Leu Asn Pro Thr Asn Glu
        370                 375                 380
Asn Gln Phe Ile Ser Gly Ser Ile Asp Gly Lys Ile Arg Val Trp Asp
385                 390                 395                 400
Ile Pro Arg Cys Ser Val Ile Asp Trp Val Asp Ile Arg Asp Ile Ile
                405                 410                 415
Thr Ala Val Cys Tyr Arg Pro Asp Gly Lys Gly Ala Val Val Gly Thr
                420                 425                 430
Ile Thr Gly Asn Cys Arg Phe Tyr Asp Ala Ser Asp Asn Leu Leu Arg
            435                 440                 445
Phe Glu Thr Gln Val Ala Leu Ser Gly Lys Lys Ser Ser Leu Lys
            450                 455                 460
Arg Ile Thr Ala Phe Glu Phe Ser Pro Ser Asn Pro Ser Lys Leu Met
465                 470                 475                 480
Val Thr Ser Ala Asp Ser Lys Val Lys Ile Leu Glu Gly Thr Thr Val
                485                 490                 495
Thr Gln Asn Tyr Ser Gly Leu Arg Thr Gly Ser Cys Gln Ser Leu Ala
                500                 505                 510
Thr Phe Thr Pro Asp Gly Gln His Ile Val Cys Ala Ser Glu Asp Ser
            515                 520                 525
Asn Ile Tyr Val Trp Asn His Glu Asn Gln Asp Glu Ala Ser Leu Lys
530                 535                 540
His Ala Lys Thr Ile Trp Ser Ser Glu Arg Phe Tyr Ser Asn Asn Ala
545                 550                 555                 560
Ala Ile Ala Ile Pro Trp Asn Gly Pro Lys Pro Arg Asn Pro Val Ser
                565                 570                 575
Leu Ala Ser Gln Ile Leu Ser Pro Gln Gly Asp Asn Leu Trp Cys Met
            580                 585                 590
Ser Lys Ala Val Lys Cys Ser Ser Gln Ser Glu Asp Ser Ala Ile
            595                 600                 605
Asn Ser Phe Val Ser Arg Phe Ala Pro Gly Ile Phe Asn Leu Asn Gln
        610                 615                 620
Glu Phe Ser Ser Glu Ser Thr Cys Arg Ser Ser Ala Thr Trp Pro Glu
625                 630                 635                 640
Glu Ile Leu Pro Ser Arg Ser Ile Arg Ala Ile Leu Asp Glu Ser Gln
                645                 650                 655
Tyr Lys Phe Leu Arg Asn Cys Phe Gln Ser Thr Pro Asn Ser Trp Gly
                660                 665                 670
Gln Val Ile Val Thr Ala Gly Trp Asp Gly Lys Ile Arg Ser Phe Gln
            675                 680                 685
Asn Tyr Gly Leu Pro Ala His Gln
```

690                695

<210> SEQ ID NO 2
<211> LENGTH: 7421
<212> TYPE: DNA
<213> ORGANISM: Maize

<400> SEQUENCE: 2

| | | | | | |
|---|---|---|---|---|---|
| gatctagctg | atcattagta | gatgacagct | agcgaacgag | cagttgtccg | accggtcctc | 60 |
| caacgagata | cggttcaatt | aaggcaacca | cgaccggtgt | ttcctctagc | ccagccccttt | 120 |
| tggacagaac | gttgttaact | ggactagcta | gcagtatgta | ttttgttgtc | actgtcagag | 180 |
| tgaaggagac | agcacacagg | aataaactgg | ctacgttgtt | caaactgaac | ggcagaacac | 240 |
| cagagaagat | ggaactctga | ctagacctct | gctttcgctg | aatggcggga | ataattcaag | 300 |
| tccggatgaa | atctgtattc | gagaattaaa | atatctggcg | acaaaacta | gatgcttgcc | 360 |
| gccccatctt | ttagaaggaa | aaaagaaag | aaagaaagc | agtggacacc | tgatcaacta | 420 |
| ccgagcctgc | ttcggtgccg | tgaccgggaa | atctttcgga | gcaggaggag | gctctccgtg | 480 |
| tccgtacgtc | ccaacggagg | tggtagaccg | agacgccgga | taagtctaag | gacgaaattt | 540 |
| agtgaccaga | gattacgaga | ggatcgaggg | attaaaaaga | aataaactac | cctttaatcc | 600 |
| tctaatcctc | ttgtaatctc | gttgtcacca | aatcaaccag | ctggtaaacc | tcccttccct | 660 |
| cccaggctcc | cagcagagag | cagcagcttt | cgtgcaaaga | tgggcacgtg | gataaaatag | 720 |
| atataaacaa | aacacaaagg | cttggacgca | tggggttgct | gccgtgccgc | cctcgcgctc | 780 |
| gcgttgccat | cttcgcccaa | ccacgaatca | actctggagc | tgcagggttg | ttggggttag | 840 |
| ctagagatgg | atacgtcgtc | catgcatctg | ctcatgcata | tccagctggg | ttctttaaac | 900 |
| tagcggacgt | acagctcgaa | tctacgtact | tagcccatta | tcagcaccta | tctttgtgtt | 960 |
| tttttcccca | gtctgctcac | tcatgtatca | aaagccacca | cacatgcaga | gcaggtggct | 1020 |
| gcgttccatg | catgcagagt | ttttttaac | gtcactgctg | accgatgcgt | ctttagggcc | 1080 |
| cgtatgtaat | ccagcttatt | ttatataaat | tatataatct | ggattgtgta | atctagttta | 1140 |
| tataatccta | ttacagatgt | ttgtttacat | aaattattag | tagataaaaa | gctaaacaat | 1200 |
| aatctaaaat | aagcatctac | taatttattt | atgaattatc | ataacctaga | catctagatt | 1260 |
| atataattca | ctccaatacc | tagagccggc | tagccgctgc | aacgactgtt | aataaataaa | 1320 |
| taaattccct | cgtccaaaaa | gggctggaat | tgatgcaggc | taaaatcaaa | atgctcggca | 1380 |
| ctactgaccg | tctgacccga | acacagacag | agcagcagcc | ccagctgacg | ggttgaccca | 1440 |
| gaccgagtcg | ccactcgcca | acaagagatc | gagctctgtg | aaatagtttt | gacgtgttcc | 1500 |
| cgttttttt | ttcttttcct | tgcgtgaata | ggtaaaagaa | gaaatcgcac | cgcgcgcctg | 1560 |
| catcctgcac | ctgtacgcgc | aaggggggac | caagcagcgg | acgcagtag | catgttaggt | 1620 |
| gcatcaaact | gttcccctcc | ccgctttga | tgagcgcctt | tgtttggcgc | aacgcgagcg | 1680 |
| cccagcccag | ctagtaattt | gccgtttcca | agcaacactt | tgcagctgca | gagcacacaa | 1740 |
| cacaagctag | ctagagtcag | atttgtgcca | acatacatat | acatgtgttc | cccttcgtc | 1800 |
| gctgctcaga | accaacggca | gggatcgatc | gtagtagtaa | tcctcctact | ctcgttcgtt | 1860 |
| ctgcccaatg | cagagccgag | cagtactgta | ctgtgctgtt | tctgttacaa | ttcactgcca | 1920 |
| cgacgaatgg | ctcgtgtcgt | ggcatgcagg | ccatgcgcct | gctgttgcta | atgctaacct | 1980 |
| cagcacatcg | gttttccaca | gcagaaaaaa | agatctcttt | ctctctgcgg | acggtcctat | 2040 |
| caggcaaggg | ttacacgagc | agatcggtgt | gctgcagcgc | cgatgcaccc | ggttgcagta | 2100 |

```
cgcatagacc caggcctaga cctgcacgat ttattgccgc tgctactaca gcagctcacc    2160
acctattact gctacaaaac gacgaccgga agtgagacga aaaggagaga aaaaacatac    2220
ataccgaaga acagaagaac aaaggaaaga taaaaagaaa ggaaagtgtg agaggcgtca    2280
tcagagggtg tgagatgaac caacccagca gcaagaaatg attaagaggc aagaggcaaa    2340
tctgcgacag tgcattgttt tagcgggaac tgtgcagtat tttcctcgtt tttttccctc    2400
tgagcagcac agtgcatctt cagaaattta tttttgcgtc cgtcctccaa atctggcgat    2460
ggtgatgggg gactcggacg ggactgggac ccccacacac ccagcacggc tggccagctc    2520
ctctcctcct cctcctccgc ctcccacgtc cgtcgtaata aatcgccccg tcgtctccaa    2580 ttcccccccct cctctccttt ctccccgccc gcgtgagatc ggctcgaatc caatcctctc    2640
caataatacg caccggcacc catttgcgcc atgctgccgc ggccggccac cacgacgagc    2700
caagaacacg cgcggcatcc ctgagccacc cacccaggct taccaaaacg gattcctttt    2760
ccctcttgga tcccagccgc tcccaagcgt gcgcgcgaat tctctgcttg cctcgcccag    2820
gtgagcttct cccccacccc cccacccctg ccatcagttt cttccttttc taatccctca    2880 ttattcccccc tctaccatca tcaatcaatc tattggtttc gacgagatat gtggtggtga    2940
attcggcggg tcttgagagg gggaagggat ttttaaaaaa aaaaccctga aattttgtca    3000
gcggttcctt ggcctggctg cccgctttaa taatggccgc gcggctggtt ggcttgccag    3060
gccagatgca ttgctcagga ggcaggagcg cttgggccgt gcgagctgcg ggatttggga    3120
gatgcgtgca gttgaatgcg tgggattcgc cgtgatttgt ttatgctgat cgccctctcc    3180
tcccgacccg tgctccctcc gcgtccgctc tctcccttttt tctcgtcccc agttgccgcc    3240
gagccaattc agcgccgctt tactgttata taagccgcgc ctccgcaccg gaccagggct    3300
ctgagatgtg tttatctttc tctcctcgca gcgccgtgtg ctcttgtgct gaagatccat    3360
cccatccatg gaagggtgcc aactgctagt aggcctagg atggagatgg aggaggaagc    3420
gttctttgac tcgcgagagg agctcacggc gtcgccggcg cccagcccgg gccctgcatt    3480
gccgtggtcg ggaagcctcg acagtgtgtg tcagaggagg gagcggttca tgagaagcat    3540
gggcctagag tgctgcccgg ctcccctgca ggccgatgcc gtgccaccg tgggcgatgt    3600 cgacaaggag gaagaggctg tgccggaatt tgggagatcg tggtcgcagt cggatgagaa    3660
cgactgctcc atgtcgagtt ggtccacgga ggagacgaag agcttagagg atggtgtctc    3720
ggatgacaat tctgtcagtg gatccagccg ggatgatgct agcagcaagg tgagcaggag    3780
tttcagttcg ttgtccttca tccagaggct catgagccgc agtggtaagc tctctggtgt    3840
tcccaaggcg gtcgagagga ggagaaacgg atggcttcgg aggctgggct gaggtctgg    3900 tatcctcgat catggaggcg atgaggctag caccagctcc tcagagagtg agcaaaacag    3960
gggtggaagg tatgaaaggg tcaaggtccg cagctacagg aagcggtcga agaactgtc    4020 agcagtttat caaggccaag tgattaaggg ccatgatggt gccatcctgg ctatgaagtt    4080
tagtccggat gggcagtttc ttgctactgg aggggaagat ggagttgtca gggtctgggg    4140
cgtcgcgcag tctgaggact gcaaaatccc aatggatgat ccttcttgtg tttacctcaa    4200
agctcatcgc cagagtggct tgggtcctgt tgatgctgac aatgagaaga aatgcaaagt    4260
taagggcgtg aagcaatctg cagattctgc ctgtgttgtg attccaacag tggtgttcca    4320
gatctcaaag caaccactgc atgagttccg tggtcactct ggtgacgtac tgagtctgtc    4380
atggtctaac aacaaggtca gtacaattat tgaatgaatt gccccctct gtaaggtttg    4440
```

```
attgcatttt tttatttatt ttgtcctttc ctttctgatg attgaaattt tctaccttgc    4500
agcatctact gtcagcatca acagacaaat ctgttcgctt gtgggaaatt ggatctgcaa    4560
actgcatcac tgttttttccg cacagcaact ttggtaggtc tatagtctct tacttgctgc   4620
tccaaaactt ttcaactatg cttctgaatt tgacctcacc atttcgctat gaaaatttac    4680
ttttgcagtg acttgtgtcc agttgaatcc aaccaatgag aatcaattca tcagtggatc    4740
catagatggc aaaatccgtg tgtgggatat tcccagatgc agtgtcattg attgggtgga    4800
tattagagac ataataacag cggtttgcta tcgacctgac ggaaaggtat cagcatgcat    4860
tctgaagtgg ggttttttatg gctaacttgt tatttcagtg gtttgtgaga ttgattttct   4920 ctgtcttttta tatcttgcag ggagcagtgg tcggaaccat tactggaaat tgtcgatttt    4980
atgatgcatc aggtacaaaa aaaaaagtga aatctctact agcttttcgt taccatttca    5040
gtacctctct gcttttactt gaatgatact ccataaatac tgactataac tacatcttga    5100
tggatcagat aatctcctga ggtttgaaac acaagttgca ctcagtggca agaaaaagtc    5160
ttctcttaaa agaatcactg ctttcgaggt aaatatcttg acgagaagga aggcttttat    5220
tgcacagttc acttcatcag tcattttttt cgctcgtatg ttctgactgt ttatttatt    5280 tttcatgtca gttctcacca agcaacccaa gtaaattaat ggttacctct gctgactcga    5340
aggttaaaat tcttgaagga accactgtga ctcagaatta tagtggtact ttccacatgc    5400
ttagctttca ttcttattga tctaagcaat cgatacattt tatgtattat gagctcatca    5460
ttttattcat tcaatcagga ctccgtactg ggtcttgcca gtccttggca acattcactc    5520
ctgatgggca gcatatagtt tgtgcaagcg aagactccaa tatttatgta tggaaccatg    5580
aaaaccaaga cgaggcttca ctgaaacatg cgaaaccat atggtcctca gagcgcttct    5640
actccaacaa tgcagccatc gcaataccat ggaatggccc gaaacccaga aacccggtct    5700
ctctggcctc ccaaatcttg tcaccacaag gagataactt gtggtgcatg agtaaggctg    5760
tcaagtgcag ttcgagtcag agcgaagatt ctgctatcaa cagttttgtg tcaaggtttg    5820
ctcctggtat tttcaatttg aatcaggagt tctcctctga gtccacttgc agaagttcag    5880
cgacctggcc agaggaaatc ctgccgtctc gctcgattcg tgcaattctg acgagtcgc    5940 agtacaagtt cctaaggaac tgtttccaga gcacaccaaa ctcgtggggt caagtgatag    6000
tcactgcagg atgggatggc aagatcaggt cgttccagaa ctatggctta ccggcgcacc    6060
agtgaacaac agctggagca tctgctgaaa ctacaccggc agttttggca cctcacatgg    6120
cgtgtggttt gttggtacaa gacatacacat gctcagtgct cctcctgctg aattgtacat    6180
ggaccagtgt tgtacataat caacctggtg gtcctttgag atctccgcgt cagcggttgt    6240
tcatggcagg acccgtggat tgtaccttt tgtagaaatt ttttgtgtgt agatcagatc    6300
tgactctctc ccttttgcccc cccttatcaa ttgctcattg atatatatac tacagaaatg    6360
ttagtctcag ctgagtgtaa gttcccctcc cattgtattg cgggaacagc cagatatata    6420
tatgtgccac tcaagtatac aaaattcttt cattttttttt tgaacttttc ctgctctgtt    6480
gttctgcaag ttttcatttt gtcgatcgaa tttcagatac aggtgactag ttctcctgtt    6540
tgacatcgta agcagttggg tgcggaccca gggaaaccgc tcttaggctg ttgacctttg    6600
attggtttgc cacgttagtt gggcatccca gaaagctgcc gatccctgat cctgaatccg    6660
ctaataattt gagctcagac ctagcattat ctgatgaatg tgctgttgtt tgtttccaag    6720 atatttttttc cacccccgtg ccgtgttgat ctgataaaga tatgcaaaaa ttatggctgg    6780
aagtatgtaa caagaacccc attttgctgc tagcacgttg ctactcattg ttgcgtttct    6840
```

```
cattttcccc tggaggttga gttccctgct gttctgaggc tggcaagcct ccccccacc     6900 cccaaatgca tgtggtcgtc atttcattcg tcgggacgtc aatggattca actcactaaa    6960
aaccatcaga gatgccgcaa ttggatcgag gcaagcgcga tcattgattg cctctaaaat    7020
actagtagta aacaacttgg ccatgattgg cgatcctggt tttttttttg tcaaacatta    7080
ggttactcag tctgcatggt tgactaatgt atgtccaatg caaggtagaa caatgggatt    7140
ttcgacctct cctgctgctt ggggggggcac ttgtagactt gtagtgtcag cggtgacgcc   7200
atgctgacat ctgatctgac actgcgacga ttactggtac aggaaattcg tctcacggtc    7260
cgcaggagac ttcactgctg cccagaatca aggctcgtaa gttccgtagt tcgattacaa    7320
attacttggg attgattttt gcagcttaac atcgtaaagc ctgagtactc tgaccacgac    7380
aaaaaaaaaa actaagacaa aaaaaaattg ttttgaagct a                        7421

<210> SEQ ID NO 3
<211> LENGTH: 2853
<212> TYPE: DNA
<213> ORGANISM: Maize

<400> SEQUENCE: 3
aggccagatg cattgctcag gaggcaggag cgcttgggcc gtgcgagctg cgggatttgg      60
gagatgcgtg cagttgaatg cgtgggattc gccgtgattt gtttatgctg atcgccctct     120
cctcccgacc cgtgctccct ccgcgtccgc tctctccctt tttctcgtcc ccagttgccg     180
ccgagccaat tcagcgccgc tttactgtta tataagccgc gcctccgcac cggaccaggg     240
ctctgagatg tgtttatctt tctctcctcg cagcgccgtg tgctcttgtg ctgaagatcc     300
atcccatcca tggaagggtg ccaactgcta gtaggctgta ggatggagat ggaggaggaa     360
gcgttctttg actcgcgaga ggagctcacg gcgtcgccgg cgcccagccc gggccctgca     420
ttgccgtggt cgggaagcct cgacagtgtg tgtcagagga gggagcggtt catgagaagc     480
atgggcctag agtgctgccc ggctcccctg caggccgatg ccgtggccac cgtgggcgat     540
gtcgacaagg aggaagaggc tgtgccggaa tttgggagat cgtggtcgca gtcggatgag     600
aacgactgct ccatgtcgag ttggtccacg gaggagacga agagcttaga ggatggtgtc     660
tcggatgaca attctgtcag tggatccagc cgggatgatg ctagcagcaa ggtgagcagg     720
agtttcagtt cgttgtcctt catccagagg ctcatgagcc gcagtggtaa gctctctggt     780
gttcccaagg cggtcgagag gaggagaaac ggatggcttc ggaggctggg cttgaggtct     840
ggtatcctcg atcatggagg cgatgaggct agcaccagct cctcagagag tgagcaaaac     900
aggggtggaa ggtatgaaag ggtcaaggtc cgcagctaca ggaagcggtc gaaagaactg     960
tcagcagttt atcaaggcca agtgattaag ggccatgatg tgccatcct ggctatgaag     1020 tttagtccgg atgggcagtt tcttgctact ggagggaag atggagttgt cagggtctgg     1080
ggcgtcgcgc agtctgagga ctgcaaaatc ccaatggatg atccttcttg tgtttacctc    1140
aaagctcatc gccagagtgg cttgggtcct gttgatgctg acaatgagaa gaaatgcaaa    1200
gttaagggcg tgaagcaatc tgcagattct gcctgtgttg tgattccaac agtggtgttc    1260
cagatctcaa agcaaccact gcatgagttc cgtggtcact ctggtgacgt actgagtctg    1320
tcatggtcta acaacaagca tctactgtca gcatcaacag acaaatctgt tcgcttgtgg    1380
gaaattggat ctgcaaactg catcactgtt tttccgcaca gcaactttgt gacttgtgtc    1440
cagttgaatc caaccaatga gaatcaattc atcagtggat ccatagatgg caaaatccgt    1500
```

```
gtgtgggata ttcccagatg cagtgtcatt gattgggtgg atattagaga cataataaca    1560
gcggtttgct atcgacctga cggaaaggga gcagtggtcg gaaccattac tggaaattgt    1620
cgattttatg atgcatcaga taatctcctg aggtttgaaa cacaagttgc actcagtggc    1680
aagaaaaagt cttctcttaa aagaatcact gctttcgagt tctcaccaag caacccaagt    1740
aaattaatgg ttacctctgc tgactcgaag gttaaaattc ttgaaggaac cactgtgact    1800
cagaattata gtggactccg tactgggtct tgccagtcct tggcaacatt cactcctgat    1860
gggcagcata tagtttgtgc aagcgaagac tccaatattt atgtatggaa ccatgaaaac    1920
caagacgagg cttcactgaa acatgcgaaa accatatggt cctcagagcg cttctactcc    1980
aacaatgcag ccatcgcaat accatggaat ggcccgaaac ccagaaaccc ggtctctctg    2040
gcctcccaaa tcttgtcacc acaaggagat aacttgtggt gcatgagtaa ggctgtcaag    2100
tgcagttcga gtcagagcga agattctgct atcaacagtt ttgtgtcaag gtttgctcct    2160
ggtattttca atttgaatca ggagttctcc tctgagtcca cttgcagaag ttcagcgacc    2220
tggccagagg aaatcctgcc gtctcgctcg attcgtgcaa ttctggacga gtcgcagtac    2280
aagttcctaa ggaactgttt ccagagcaca ccaaactcgt ggggtcaagt gatagtcact    2340
gcaggatggg atggcaagat caggtcgttc cagaactatg gcttaccggc gcaccagtga    2400
acaacagctg gagcatctgc tgaaactaca ccggcagttt tggcacctca catggcgtgt    2460
ggtttgttgg tacaagacat acatgctcag tgctcctcc tgctgaattg tacatggacc    2520
agtgttgtac ataatcaacc tggtggtcct ttgagatctc cgcgtcagcg gttgttcatg    2580
gcaggacccg tggattgtac ctttttgtag aaatttttg tgtgtagatc agatctgact    2640 ctctccctt gccccccctt atcaattgct cattgatata tatactacag aaatgttagt    2700
ctcagctgag tgtaagttcc cctcccattg tattgcggga acagccagat atatatatgt    2760
gccactcaag tatacaaaat tctttcattt tttttgaac ttttcctgct ctgttgttct    2820
gcaagttttc attttgtcga tcgaatttca gat                                 2853

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
cacaagacta caaggacgag a                                              21

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
ggcaggaagg aggaagaaga                                                20

<210> SEQ ID NO 6
<211> LENGTH: 18
<212> TYPE: DNA
<213> ORGANISM: Artificial sequence
<220> FEATURE:
<223> OTHER INFORMATION: Primer

<400> SEQUENCE: 6
```

```
ccgcaaatct ccgcacac                                                     18

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
tgatccaccg ccaaaataca g                                                 21

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
taagggtgcg aatggaaag                                                    19

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
gggggacacg tcgtaggt                                                     18

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
gctcgttccg tagtgtagtc tg                                                22

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
cagaaccacg actatttatc cg                                                22

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
atgtctccca ctgctgctac                                                   20

<210> SEQ ID NO 13
<211> LENGTH: 19
<212> TYPE: DNA
```

```
<213> ORGANISM: Artificial sequence
<220> FEATURE:
<223> OTHER INFORMATION: Primer

<400> SEQUENCE: 13
cctccgtgac ctcatcgtc                                                   19

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
agttgatcgc tcgtcctg                                                    18

<210> SEQ ID NO 15
<211> LENGTH: 18
<212> TYPE: DNA
<213> ORGANISM: Artificial sequence
<220> FEATURE:
<223> OTHER INFORMATION: Primer

<400> SEQUENCE: 15
tgtcaggtga cccatccc                                                    18

<210> SEQ ID NO 16
<211> LENGTH: 18
<212> TYPE: DNA
<213> ORGANISM: Artificial sequence
<220> FEATURE:
<223> OTHER INFORMATION: Primer

<400> SEQUENCE: 16
acgggcgacg agaagaac                                                    18

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
cagcatcaga ccctcactac c                                                21

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
taggctgtag gatggagatg                                                  20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
gaccttgacc ctttcatacc                                                  20
```

<210> SEQ ID NO 20
<211> LENGTH: 25
<212> TYPE: DNA
<213> ORGANISM: Artificial sequence
<220> FEATURE:
<223> OTHER INFORMATION: Primer

<400> SEQUENCE: 20
cgcctccatt tcgtcgaatc cccts                                   25

<210> SEQ ID NO 21
<211> LENGTH: 2693
<212> TYPE: DNA
<213> ORGANISM: Rice

<400> SEQUENCE: 21

| | | | | | | |
|---|---|---|---|---|---|---|
| atggagggt | gccaattggt | agcgaggtgt | agtagtagta | gtagcagtag | caggatggag | 60 |
| gtggaggaag | aggcgttctt | tgacacgcgg | gaggagctgc | tgccgccgtc | gccggcggcg | 120 |
| gcattgccgt | ggtcgggtgg | gctcgacagc | gtgcggcagc | ggagggagcg | gttcatgcga | 180 |
| agcatgggcc | tggagcgcag | cccgagcctc | cgccaggcgg | atttcgcgga | cgtcgtgggc | 240 |
| gatgtggagg | aggagggtga | ggtggcggcg | gaggcggaga | tcgggaggtg | gtcgtcgcag | 300 |
| tcggacgaga | acgagtgctc | catgtcgagc | tggtcgacgg | aggagacgac | gagctacgac | 360 |
| gacggcgcgt | cggatgacaa | ctccgtgagt | ggatccggca | aggcgagcag | gagcttcagc | 420 |
| tcgctgtcgt | tcatccagag | gctcatgagc | cgcaatggca | agccttctgg | tgctccgaag | 480 |
| acgatcgaca | ggaggagaaa | tgggtggctc | cggaggctgg | gcgtcagtgc | ttgtgttgtg | 540 |
| gatagtggag | cagcagatga | agccagcacc | agttcttcag | atagtgagca | aattggggct | 600 |
| gggaggtatg | aaagaatcaa | ggttcactcg | taccggaagc | ggtcgaagga | attgtccgcc | 660 |
| gtgtatcagg | ggcaagtgat | caaagcacat | gatggtgcca | tcctgacgat | gaagtttagt | 720 |
| cctgatgggc | agcttcttgc | aaccggtgga | gaagatggag | ttgtcagggt | ttgggctgtc | 780 |
| atgcagtccg | aggactgcaa | aattccactg | gatgatcctt | cttgcgtcta | cctaaaagcg | 840 |
| cggcgcaagt | atgggcttgc | tcctgtgaat | gccgagagcg | agaagaaatc | gaagatcaat | 900 |
| ggcctgaaaa | aatccgattc | tgcttgtatt | gtggttccaa | cgatggtttt | ccagatctca | 960 |
| gaggaaccag | tgcatgagtt | ccgtgggcac | tctggtgatg | tgcttgattt | gtcatggtcg | 1020 |
| agcgataagg | ttagttaatg | aaatgctctt | ttgtccatgt | attggaattg | ttcctttgcg | 1080 |
| tttttcctta | tgctgtactt | tttggttctg | ataattaata | tttgctactt | tacagcatct | 1140 |
| actgtcagca | tcaacagaca | aaactgttcg | catgtgggaa | attggatatg | caaactgcat | 1200 |
| cagagtttat | ccacatagca | actttggtag | gtttatgtga | tcctactag | ctgcctcaaa | 1260 |
| ggtcttcact | ttcatctata | aatttgagct | aacttttttt | tcttgtttta | cagtgacttg | 1320 |
| tgtccaattt | aatctagctg | acgagaatct | cttcattagt | ggatcaattg | atggcaaaat | 1380 |
| tcgtgtttgg | gacattacta | gaagcagtgt | tgtggactgg | gtggatatta | gagacatagt | 1440 |
| aacagcagtt | tgttaccggc | ctggtggaaa | ggtatgatta | tcagcggcca | tcttagctgt | 1500 |
| tttgactaac | ttgctgcgtc | agtaatttgt | gatactgatg | tcctttcttt | tcgaatatct | 1560 |
| tgcagggagt | ggtggttggt | actattactg | gaaattgtcg | cttctatgaa | atatctggtt | 1620 |
| agtactaaac | actaaattgc | caaatgatta | ttagctttaa | aatatatttt | tgataggcag | 1680 |
| aatacgtgtt | tatacttatg | cttatttcat | ctgttttgca | ttggatcaga | caatctgctg | 1740 |

-continued

| | |
|---|---|
| aagctagaaa cacaaattgc tctcaatgga aagaagaaat catctctcaa aagaatcaca | 1800 |
| ggctttcagg taacatcttg ggcaaggaag aggcatgctg taatcaataa attcatcagt | 1860 |
| ccttttttcac tagaaatcct tccgactctt ttttttcctca ttcccattgc agttttgccc | 1920 |
| aagcaaccca agtaaactaa tggtgacatc tgccgattcg aagatcagaa tacttgatgg | 1980 |
| gaccaatgtg attcagaatt atagtggtac acccaaatac tcgtttatta tttctgctct | 2040 |
| atctagtcat ttcctgggta ttcggatgga taatttttt tttttttgct aatctatcag | 2100 |
| gactccgaag tggttcttgc cagttgtcag caacattcac tccagaaggg cagcacataa | 2160 |
| tttctgccag tgaagactcc aacgtttatg tttggagcca tgaaaaccag tatgagtgtg | 2220 |
| catgcaaaca agcaaaaacc acacagacat ctgagcattt ccggtccaac aatgcagcca | 2280 |
| ttgcaatacc atggaatggc acaaaaccaa gaagcccagt tccgttgtcg tcccaaattt | 2340 |
| taccaccaca aggagatact ttctggtcaa tgagcaaggc tatcaaatac aattcaagcc | 2400 |
| tctgtggaaa ggattcttcc attaaaaaaa ttgtgtcaac gcctgctgct cctggtattt | 2460 |
| tcaatctgaa ccaggagttc ttcattgagt cctcttgcaa aagttcagca acttggccag | 2520 |
| aggaaatgct accatctacc acagccagtg taaatttgga cgagtcacag ttcaagctct | 2580 |
| taaggaactg tttccaagga acatcaaact cctggggtca agtgatagtt actgcaggat | 2640 |
| gggatggcag gattaggtat ttccagaatt tcggtttacc agtgcatcag tga | 2693 |

<210> SEQ ID NO 22
<211> LENGTH: 2097
<212> TYPE: DNA
<213> ORGANISM: Rice

<400> SEQUENCE: 22

| | |
|---|---|
| atggaggggt gccaattggt agcgaggtgt agtagtagta gtagcagtag caggatggag | 60 |
| gtggaggaag aggcgttctt tgacacgcgg gaggagctgc tgccgccgtc gccggcggcg | 120 |
| gcattgccgt ggtcgggtgg gctcgacagc gtgcggcagc ggagggagcg gttcatgcga | 180 |
| agcatgggcc tggagcgcag cccgagcctc cgccaggcgg atttcgcgga cgtcgtgggc | 240 |
| gatgtggagg aggagggtga ggtggcggcg gaggcggaga tcgggaggtg gtcgtcgcag | 300 |
| tcggacgaga acgagtgctc catgtcgagc tggtcgacgg aggagacgac gagctacgac | 360 |
| gacggcgcgt cggatgacaa ctccgtgagt ggatccggca aggcgagcag gagcttcagc | 420 |
| tcgctgtcgt tcatccagag gctcatgagc cgcaatggca agccttctgg tgctccgaag | 480 |
| acgatcgaca ggaggagaaa tgggtggctc cggaggctgg gcgtcagtgc ttgtgttgtg | 540 |
| gatagtggag cagcagatga agccagcacc agttcttcag atagtgagca aattggggct | 600 |
| gggaggtatg aaagaatcaa ggttcactcg taccggaagc ggtcgaagga attgtccgcc | 660 |
| gtgtatcagg ggcaagtgat caaagcacat gatggtgcca tcctgacgat gaagtttagt | 720 |
| cctgatgggc agcttcttgc aaccggtgga aagatggag ttgtcagggt ttgggctgtc | 780 |
| atgcagtccg aggactgcaa aattccactg gatgatcctt cttgcgtcta cctaaaagcg | 840 |
| cggcgcaagt atgggcttgc tcctgtgaat gccgagagcg agaagaaatc gaagatcaat | 900 |
| ggcctgaaaa aatccgattc tgcttgtatt gtggttccaa cgatggtttt ccagatctca | 960 |
| gaggaaccag tgcatgagtt ccgtgggcac tctggtgatg tgcttgattt gtcatggtcg | 1020 |
| agcgataagc atctactgtc agcatcaaca gacaaaactg ttcgcatgtg gaaattgga | 1080 |
| tatgcaaact gcatcagagt ttatccacat agcaactttg tgacttgtgt ccaatttaat | 1140 |
| ctagctgacg agaatctctt cattagtgga tcaattgatg gcaaaattcg tgtttgggac | 1200 |

```
attactagaa gcagtgttgt ggactgggtg gatattagag acatagtaac agcagtttgt      1260
taccggcctg gtggaaaggg agtggtggtt ggtactatta ctggaaattg tcgcttctat      1320
gaaatatctg acaatctgct gaagctagaa acacaaattg ctctcaatgg aaagaagaaa      1380
tcatctctca aaagaatcac aggctttcag ttttgcccaa gcaacccaag taaactaatg      1440
gtgacatctg ccgattcgaa gatcagaata cttgatggga ccaatgtgat tcagaattat      1500
agtggactcc gaagtggttc ttgccagttg tcagcaacat tcactccaga agggcagcac      1560
ataatttctg ccagtgaaga ctccaacgtt tatgtttgga gccatgaaaa ccagtatgag      1620
tgtgcatgca aacaagcaaa aaccacacag acatctgagc atttccggtc caacaatgca      1680
gccattgcaa taccatggaa tggcacaaaa ccaagaagcc cagttccgtt gtcgtcccaa      1740
attttaccac cacaaggaga tactttctgg tcaatgagca aggctatcaa atacaattca      1800
agcctctgtg gaaaggattc ttccattaaa aaaattgtgt caacgcctgc tgctcctggt      1860
attttcaatc tgaaccagga gttcttcatt gagtcctctt gcaaaagttc agcaacttgg      1920
ccagaggaaa tgctaccatc taccacagcc agtgtaaatt tggacgagtc acagttcaag      1980
ctcttaagga actgtttcca aggaacatca aactcctggg gtcaagtgat agttactgca      2040
ggatgggatg gcaggattag gtatttccag aatttcggtt taccagtgca tcagtga        2097
```

```
<210> SEQ ID NO 23
<211> LENGTH: 19
<212> TYPE: DNA
<213> ORGANISM: Artificial sequence
<220> FEATURE:
<223> OTHER INFORMATION: gRNA-KRN2-1

<400> SEQUENCE: 23
ggccctgcat tgccgtggt                                                   19

<210> SEQ ID NO 24
<211> LENGTH: 19
<212> TYPE: DNA
<213> ORGANISM: Artificial sequence
<220> FEATURE:
<223> OTHER INFORMATION: gRNA-KRN2-2

<400> SEQUENCE: 24
agagtgctgc ccggctccc                                                   19

<210> SEQ ID NO 25
<211> LENGTH: 20
<212> TYPE: DNA
<213> ORGANISM: Artificial sequence
<220> FEATURE:
<223> OTHER INFORMATION: gRNA-KRN2-2

<400> SEQUENCE: 25
aggttcactc gtaccggaag                                                  20
```

MAIZE GENE *KRN2* AND USES THEREOF

CROSS-REFERENCE TO RELATED APPLICATIONS

This application is a U.S. national stage filing, under 35 U.S.C. § 371(c), of International Application No. PCT/CN2018/117844, filed on Nov. 28, 2018, which claims the benefit of priority to Chinese Patent Application No. 201711217216.3, filed on Nov. 28, 2017. The entire contents of each of the aforementioned applications are incorporated herein by reference.

FIELD OF INVENTION

The present invention relates to the field of plant genetics and molecular breeding. In particular, the present application relates to the KRN2 gene controlling kernel row number (KRN) in plant, molecular markers closely linked to KRN2 and their application in molecular breeding.

SEQUENCE LISTING

The instant application contains a Sequence Listing which has been filed electronically in ASCII format and is hereby incorporated by reference in its entirety. Said ASCII copy, created on Nov. 29, 2020 and having a size of 29,937 bytes, is named 132173_00102_SL.txt.

BACKGROUND

Maize is useful as food or feed, and is the world's largest food crop. In recent years, China's total grain output has achieved "twelve consecutive increases", and maize has played an important role. Increasing maize production has important strategic significance for safeguarding China's food security. However, with the adjustment of planting structure, China's maize planting area will show a downward trend, while the maize demand will continue to maintain a rigid growth trend with the rapid development of national economy and the continuous improvement of people's living standards. Therefore, increasing maize yield is an important way to increase the total grain yield in China. It is of great significance to study the genetic basis of maize yield trait to increase maize yield.

Maize yield is an extremely complex quantitative trait. Among the many factors that contribute to maize yield, 100-kernel weight, kernel row number, and kernel number per row are the decisive factors affecting the yield of maize. Kernel row number (KRN) refers to the number of kernel rows of the ear, which is one of the most important factors that contribute to the maize yield trait, and is significantly positively correlated with yield. KRN is a trait controlled by multiple genes or loci. In the process of domestication and genetic improvement of maize, KRN is strongly selected. Therefore, cloning of the major and minor quantitative trait loci (QTL) affecting the quantitative variation of the KRN, and subsequently understanding the genetic basis of KRN have great significance for understanding the formation mechanism of the maize yield trait and the selection mode of excellent alleles in genetic improvement. Meanwhile, it also provides important theoretical guidance for molecular breeding and genetic improvement of traits such as maize yield.

However, the maize genome is very complicated, and it is very difficult to perform map-based cloning of quantitative trait loci. The main principle of map-based cloning is to clone genes based on their relative positions on the gene map. Firstly, a primary QTL population is used to perform preliminary QTL mapping of the quantitative traits studied, and then combined with backcrossing and molecular marker-assisted selection, the target QTL is selected in the foreground when the negative selection of the background is carried out. Near isogenic lines, chromosomal fragment replacement lines or introgression lines of the target QTL are developed and used to produce larger isolated populations. Then, specific primers are designed against the target region, thus to finely locate the QTL and narrow the target QTL to a small genomic region. On such basis, the chromosomal walking method is used to construct contigs that cover the target region and to identify the candidate genes of the site. Finally, the candidate genes are analyzed and predicted for their sequence characteristics and coding products, the functions of which are further verified by expression analysis or complementary assay. Currently, the confidence interval of QTL is usually above 10 cM, which may include a major QTL or multiple micro-effect QTLs, wherein the cloning of multiple micro-effect QTLs further increases the difficulty.

Molecular breeding is currently an important route for genetic improvement of maize, and the cloning of target genes is a prerequisite for obtaining new varieties with ideal target traits through molecular breeding techniques. KRN is one of the main factors contributing to maize yield. Increasing the KRN of maize has an important role in increasing the yield. Therefore, the cloning of maize KRN-related genes can provide new genes for the breeding of high-yield varieties, which plays an important role in the genetic improvement of maize yield. Moreover, the study of g maize KRN-related genes also provides important insights for the study of traits similar to KRN or homologous genes in other crops, such as rice, wheat, barley, and sorghum.

DESCRIPTION

One object of the invention is to provide the protein KRN2 and its coding gene related to kernel row number in plants.

In one aspect, the present invention provides an isolated or purified protein, which comprises an amino acid sequence selected from a group consisting of:
 (1) an amino acid sequence as set forth in SEQ ID NO: 1; and
 (2) an amino acid sequence which has at least 70% identity with SEQ ID NO: 1 and has the activity of regulating kernel row number in plants.

In another aspect, the present invention provides a nucleic acid molecule encoding a protein which regulates kernel row number in plants. Preferably, the nucleic acid molecule comprises a nucleic acid sequence selected from a group consisting of:
 (1) a nucleic acid sequence as set forth in SEQ ID NO: 2 or 3, or a sequence complementary thereto;
 (2) a nucleic acid sequence as set forth in positions 310-2400 of SEQ ID NO: 3, or a sequence complementary thereto;
 (3) a nucleic acid sequence which has at least 70% identity with the nucleic acid sequence as set forth in SEQ ID NO: 2, SEQ ID NO: 3, or positions 310-2400 of SEQ ID NO: 3 and has the activity of regulating kernel row number in plants, or a sequence complementary thereto; and
 (4) a nucleic acid sequence which hybridizes with SEQ ID NO: 2, SEQ ID NO: 3, or positions 310-2400 of SEQ ID NO: 3 under stringent conditions and has the activity of regulating kernel row number in plants, or a sequence complementary thereto.

As used herein, the term "stringent condition" usually refers to the condition described in Sambrook et al., 1989 and Haymes et al., Nucleic acid hybridization, A practical approach, IRO Press, Washington, DC (1985). Stringent conditions suitable for DNA hybridization is known to one skilled in the art, such as wash with 6.0×sodium chloride/sodium citrate (SSC) at 45° C., followed by wash with 2.0×SSC at 50° C., or can be found in Current Protocols in Molecular Biology, John Wiley&Sons, N.Y., 1989, 6.3.1-6.3.6. For example, the salt concentration in the wash step can varies from a low stringent condition of about 2.0×SSC at 50° C. to a high stringent condition of about 0.2×SSC at 50° C. In addition, the temperature in the wash step can increases from a low stringent condition of room temperature (about 22° C.) to a high stringent condition of about 65° C. The temperature and salt both can change, or one of them remains the same while the other changes. For instance, a medium stringent condition may be a salt concentration of 2.0×SSC and a temperature of 65° C., and a high stringent condition may be a salt concentration of 0.2×SSC and a temperature of 65° C. In one embodiment, the stringent condition used for nucleic acid hybridization in the present application refers to a hybridization at 65° C. in 0.5% SDS solution, wherein the film is washed once successively with 2×SSC+0.1% SDS and 1×SSC+0.1% SDS at 65° C.

One skilled in the art knows that "kernel number per ear" or "KRN" is a quantitative trait measuring the number of kernels in an ear. Based on different forms of ears, kernel number per ear in different plants may consist of different factors. For example, in maize, wheat and barley, kernel number per ear generally consists of KRN and kernel number per row; while in rice and sorghum, this parameter consists of branch number and grain number per branch. In *Arabidopsis*, the number of grains depends on the number of inflorescence. Thus, the term "kernel row number" or "KRN" used herein not only includes the "kernel row number" trait in maize, wheat and barley, but also includes traits similar to "kernel row number" in rice and sorghum, such as "branch number", as well as similar traits in other plants, such as the number of inflorescence in *Arabidopsis*. Indeed, the internal genetic mechanism regulating the trait "kernel row number" in different plants share certain common property, for example, all involve the regulation of inflorescence development in plants (see for example Junko Kyozuka, Hiroki Tokunaga and Akiko Yoshida. Control of grass inflorescence form by the fine-tuning of meristem phase change. Current Opinion in Plant Biology 2014, 17:110-115). Accordingly, one skilled in the art can reasonably expect that the KRN2 gene according to the present invention not only can regulate kernel row number in maize, but also can regulate traits similar to "kernel row number" in other plants, such as the aforementioned kernel row number in crops such as wheat, the branch number of rice and the number of inflorescence of *Arabidopsis*.

As used herein, the term "sequence identity" refers to the extent to which two optimally aligned polynucleotide sequences or two optimally aligned polypeptide sequences are identical. Optimal sequence alignment is established by manually aligning two sequences, for example, a reference sequence and another DNA sequence, so as to maximize nucleotide match in sequence alignments with appropriate internal nucleotide insertions, deletions or gaps. As used herein, the term "reference sequence" refers to the amino acid sequence set forth in SEQ ID NO: 1 or the nucleic acid sequence set forth in SEQ ID NOs: 2 and 3, and positions 310-2400 of SEQ ID NO: 3.

As used herein, the term "% sequence identity" or "% identity" refers to the identity ratio multiplied by 100. By "identity percentage" of a sequence optimally aligned to a reference sequence, it means the number of matched nucleotides in an optimal alignment divided by the total number of nucleotides in the reference sequence, such as the total number of nucleotides in the whole full-length reference sequence. Thus, one embodiment of the present invention provides a DNA molecule comprising a sequence having at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% identity to a reference sequence when optimally aligned with said reference sequence, i.e., the amino acid sequence set forth in SEQ ID NO: 1 or the nucleic acid sequence set forth in SEQ ID NOs: 2 and 3, or positions 310-2400 of SEQ ID NO: 3.

The gene according to the present invention also includes variant sequences derived from deletion, substitution, insertion or addition in one or more nucleotides of the KRN2 gene, which maintains the regulatory activity of the KRN2 gene. Gene mutation is a sudden inheritable variable phenomenon occurred in genomic DNA molecule. At the molecular level, gene mutation refers to alteration in base pair composition or arrangement sequence occurred in gene structure. Gene mutation may be spontaneous or inducible, and methods of artificial mutagenesis include physical mutagenesis (such as gamma rays, x-rays, ultraviolet light, and neutron flux), chemical mutagenesis (such as alkylating agents, base analogs, and antibiotics) and biological mutagenesis (such as certain viruses and bacteria, etc.). Moreover, directed mutagenesis can be achieved using recombinant DNA techniques to make specific changes in DNA molecules at specific locations. Any of these well-known mutagenesis methods can be used to obtain variant sequences of the KRN2 gene comprising mutation, deletion, substitution, insertion or addition in one or more nucleotides.

Preferably, the nucleic acid molecule according to the present invention is operably linked to a heterologous promoter, to form a recombinant DNA molecule.

In another aspect, the present invention provides an expression cassette comprising the recombinant DNA molecule of the present invention, a recombinant vector comprising said expression cassette, a host cell comprising said recombinant vector, and a transgenic plant cell, transgenic plant and plant parts thereof comprising said recombinant DNA molecule.

As used herein, "plant part" includes but not limited to leaf, stem, root, tuber, seeds, endosperm, ovule and pollen. The plant part of the invention may be viable, non-viable, regenerable and/or non-regenerable. The present invention also encompasses and provides transformed plant cells comprising the DNA molecule of the invention. The transformed plant cell or transgenic plant cell of the invention comprising regenerable and/or non-regenerable plant cells.

The plant of the invention includes monocots and dicots. Specifically, the plants in which KRN2 gene expression is inhibited to increase the yield can be selected from the crop plants such as maize (corn; *Zea mays*), soybean (*Glycine max*), cotton (*Gossypium hirsutum*; *Gossypium* sp.), peanut (*Arachis hypogaea*), barley (*Hordeum vulgare*); oats (*Avena sativa*); orchard grass (*Dactylis glomerata*); rice (*Oryza sativa*, including indica and *japonica* varieties); sorghum (*Sorghum bicolor*); sugar cane (*Saccharum* sp.); tall fescue (*Festuca arundinacea*); turfgrass species (e.g. species: *Agrostis stolonifera, Poa pratensis, Stenotaphrum secundatum*), wheat (*Triticum aestivum*), alfalfa (*Medicago sativa*); *Arabidopsis* (*Arabidopsis thaliana*); members of the genus *Brassica*, including broccoli, cabbage, carrot, cauliflower, Chinese cabbage; cucumber, dry bean, eggplant, tobacco, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut.

The inventors showed that the KRN2 gene expression is negatively related to the kernel row number. Thus, by inhibiting the expression of the KRN2 gene, plants with increased kernel row number, thereby increased yield can be obtained. Accordingly, another object of the present invention is to provide a method of producing a transgenic plant with increased kernel row number or increased yield, comprising obtaining a transgenic plant cell with inhibited expression of the KRN2 gene or the gene products thereof compared to a wild type plant, and regenerating a transgenic plant from said transgenic plant cell Methods of inhibiting the expression of a target gene or gene product thereof is known in the art, such as transposon insertion, mutagenesis, RNA-mediated inhibition, gene editing and the like. In context of the present application, the term "KRN2 gene" refers to any nucleotide sequences able to produce the amino acid sequence set forth in SEQ ID NO: 1. In a preferable embodiment, KRN2 gene herein refers to the nucleotide sequence set forth in SEQ ID NO: 2, SEQ ID NO: 3 or positions 310-2400 of SEQ ID NO: 3.

In one embodiment of the method, the transgenic plant with increased kernel row number or increased yield is produced by introducing a gene mutation in the KRN2 gene that results in an inhibited expression of the KRN2 gene in a plant. Examples of gene mutation include without limitation knock-out mutation, a truncation mutation, a point mutation, a missense mutation, a substitution mutation, a frameshift mutation, an insertion mutation, a duplication mutation, an amplification mutation, a translocation mutation, or an inversion mutation, and any other gene mutation that results in a reduction or inactivation in the corresponding gene activity. Methods of generating at least one mutation in a target gene are well known in the art and include, without limitation, random mutagenesis and screening, site-directed mutagenesis, PCR mutagenesis, insertional mutagenesis, physical mutagenesis, chemical mutagenesis, and irradiation. The mutagenesis, which may be specific or random, may be performed, for example, by use of a suitable physical or chemical mutagenizing agent, use of a suitable oligonucleotide, subjecting the DNA sequence to PCR generated mutagenesis, or any combination thereof. Examples of physical and chemical mutagenizing agents include, without limitation, ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the plant cells or tissues to be mutagenized in the presence of the mutagenizing agent of choice under suitable conditions, and then selecting for mutants exhibiting reduced or no expression of the target gene.

In one embodiment of the method, the transgenic plant with increased kernel row number or increased yield is produced by RNA-mediated inhibition of the KRN2 gene expression in a plant. In particular, said RNA-mediated inhibition of the KRN2 gene expression is achieved by introducing into a plant cell a polynucleotide encoding a RNA molecule comprising a sequence that is essentially complementary to at least 15 continuous nucleotides of the KRN2 gene or fragments thereof, wherein the expression of the polynucleotide results in inhibited expression of the KRN2 gene in said plant. A construct comprising a polynucleotide encoding a RNA molecule comprising a sequence that is essentially complementary to to at least 15 continuous nucleotides of the KRN2 gene or fragments thereof, wherein the expression of the construct results in inhibited expression of the KRN2 gene in said plant is also encompassed in the scope of the invention.

In an embodiment, the above polynucleotide encoding a RNA molecule encompass oligonucleotides having a length of 15-25 nucleotides (15-mers, 16-mers, 17-mers, 18-mers, 19-mers, 20-mers, 21-mers, 22-mers, 23-mers, 24-mers, or 25-mers) or fragments thereof, or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or fragments thereof or long polynucleotides having a length greater than about 300 nucleotides (for example, polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene), wherein the polynucleotides or fragments thereof are homologous or complementary to the target KRN2 gene, and suppresses the expression of the target KRN2 gene when expressed in a plant cell.

Many RNA-mediated inhibition methods are known in the art. Non-limiting examples of RNA molecules used in the RNA-mediated inhibition methods include, but are not limited to, antisense RNAs, miRNAs, siRNAs and long non-coding RNAs. Antisense RNA is a single-stranded RNA that is complementary to a messenger RNA (mRNA) strand transcribed in a cell. When antisense RNA is expressed in a cell, it binds to a specific messenger RNA molecule and inactivates it. An siRNA is a double-stranded RNA molecule, 20-25 base pairs in length. After separating into single strands and integrating into an active RISC complex, it base-pairs to its target mRNA and induces cleavage of the target mRNA, thereby preventing it from being used as a translation template. A miRNA is a small RNA, typically about 21 nucleotides, that has the ability to modulate the expression of a target gene by binding to mRNA for the target protein, leading to destabilization or translational inhibition of the target protein mRNA, ultimately resulting in reduction of the target protein. Methods for selecting and designing siRNAs and miRNAs for gene inhibition are well known in the art. Long non-coding RNAs (long ncRNA or lncRNA) are non-protein coding transcripts longer than 200 nucleotides (Perkel, BioTechniques, 54 (6):301-304 (2013)). In contrast to many small RNAs which exhibit strong conservation across diverse species, long ncRNAs in general lack strong conservation. Long ncRNAs can be categorized, according to their proximity to protein coding genes in the genome, into five categories; sense, antisense, bidirectional, intronic, and intergenic, and regulate gene expression through a diverse group of mechanisms, such as through gene transcription (e.g., through gene-specific transcription regulation and regulation of basal transcription machinery), post-transcriptional regulation (e.g., through mRNA splicing, translation and siRNA-directed gene regulation) or through epigenetic regulation. The effect of a siRNA, a miRNA or a long non-coding RNA on target gene inhibition can be assessed by a beto-glucuronidase or uidA gene (GUS) reporter expression comparison.

The polynucleotide encoding the RNA molecule of the present invention can be single- or double-stranded RNA or single- or double-stranded DNA or double-stranded DNA/RNA hybrids or modified analogues thereof, and can be of oligonucleotide lengths or longer. In more specific embodiments of the invention, the polynucleotides that provide RNA molecule of the invention in the plant cell are selected from the group consisting of (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/DNA molecule, or combinations thereof. In some embodiments, these polynucleotides include chemically modified nucleotides or non-canonical nucleotides. In embodiments of the method, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment, the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for inhibition. In certain other embodiments, the polynucleotides further includes a promoter, generally a promoter functional in a plant, for example, a pol II promoter, a pol III promoter, a pol IV promoter, or a pol V promoter.

One skilled in the art is aware that the polynucleotides according to the invention have sequence complementarity that need not be 100 percent, but is at least sufficient to provide a RNA molecule permit hybridization to RNA transcribed from the target gene or DNA of the target gene to form a duplex to permit a gene silencing mechanism. Thus, in embodiments, a polynucleotide fragment is designed to be essentially identical to, or essentially complementary to, a sequence of 15 or more contiguous nucleotides in either the target KRN2 gene sequence or messenger RNA transcribed from the target gene. By "essentially identical" is meant having 100 percent sequence identity or at least about 70, 75, 80, 81, 82, 83, 84, 85, 86, 87, 88, 89, 90, 91, 92, 93, 94, 95, 96, 97, 98, or 99 percent sequence identity when compared to the sequence of at least 15 or more contiguous nucleotides (for example, at least 16, 17, 18, 19, 20, 21, 22, 23, 24, 25, 26, 27, 28, 29, 30 or more contiguous nucleotides) in either the target gene or RNA transcribed from the target gene; by "essentially complementary" is meant having 100 percent sequence complementarity or at least about 70, 75, 80, 81, 82, 83, 84, 85, 86, 87, 88, 89, 90, 91, 92, 93, 94, 95, 96, 97, 98, or 99 percent sequence complementarity when compared to the sequence of at least 15 or more contiguous nucleotides (for example, at least 16, 17, 18, 19, 20, 21, 22, 23, 24, 25, 26, 27, 28, 29, 30 or more contiguous nucleotides) in either the target gene or RNA transcribed from the target gene. In some embodiments, polynucleotide molecules are designed to have 100 percent sequence identity with or complementarity to one allele or one family member of a given target gene.

The methods for identifying or designing the polynucleotides of the invention are known in the art. For example, said polynucleotides can be identified by "tiling" the gene targets with partially overlapping probes or non-overlapping probes of antisense or sense polynucleotides that are essentially identical or essentially complementary to the nucleotide sequence of an endogenous gene. They also can be pooled into a few treatments in order to investigate polynucleotide molecules that cover a portion of a gene sequence (for example, a portion of a coding versus a portion of a noncoding region, or a 5' versus a 3' portion of a gene) or an entire gene sequence including coding and noncoding regions of a target gene. The pooled polynucleotide molecules can be divided into smaller pools or single molecules in order to identify effective polynucleotide molecules that provide the desired effect.

In one embodiment of the method, the transgenic plant with increased kernel row number or increased yield is produced by gene editing the KRN2 gene in a plant, thereby inhibiting the expression of the KRN2 gene in said plant.

As used herein, the term "gene editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with the endogenous nucleic acid of interest.

In a preferred embodiment, the gene editing is achieved by providing an endonuclease selected from a meganuclease, a Zinc finger endonuclease, a TALEN endonuclease or a CRISPR endonuclease. In a specific embodiment, the CRISPR endonuclease is a CRISPR/Cas9, CRISPR/Cpf1, CRISPR/CasX or a CRISPR/CasY endonuclease.

Meganucleases, found commonly in microbial species, have the unique property of having very long recognition sequences (>14 bp) thus making them naturally very specific. However, there is virtually no chance of finding the exact meganuclease required to act on a specific DNA sequence. To overcome this challenge, mutagenesis and high throughput screening methods have been used to create meganuclease variants that recognize unique sequences. Others have been able to fuse various meganucleases and create hybrid enzymes that recognize a new sequence. Yet others have attempted to alter the DNA interacting amino acids of the meganuclease to design sequence specific meganucleases in a method named rationally designed meganuclease.

Zinc finger endonucleases (ZFNs) recognize target DNA in a modular fashion: each endonuclease consists of at least three zinc finger domains, and a single zinc finger domain interacts with a 3-bp sequence, making them ideal programmable sequence-specific DNA-binding proteins TALENs emerged as a competitive alternative to ZFNs in 2011. Unlike zinc fingers, each repeat domain in TALE proteins recognizes a single base. Four different repeat domains can be mixed and matched to create new DNA-binding proteins, which can be linked to the FokI domain to create a new class of programmable target DNA nucleases. These molecules enable precise targeting and cutting at a specific genomic locus to generate double-strand breaks (DSBs) followed by non-homologous end joining (NHEJ) or homology-directed repair (HDR)-mediated repair, thereby enabling precise genome editing.

The Clustered Regularly Interspersed Short Palindromic Repeats (CRISPRs) system constitutes an adaptive immune system in prokaryotes that targets endonucleolytic cleavage of invading phage. The CRISPR systems rely on small RNAs for sequence-specific detection and targeting of foreign nucleic acids for destruction. The components of the bacterial CRISPR systems are CRISPR-associated (Cas) genes and CRISPR array(s) consisting of genome-target sequences (protospacers) interspersed with short palindromic repeats. Transcription of the protospacer/repeat elements into precursor CRISPR RNA (pre-crRNA) molecules is followed by enzymatic cleavage triggered by hybridization between a trans-acting CRISPR RNA (tracrRNA) molecule and a pre-crRNA palindromic repeat. The resulting crRNA:tracrRNA molecules, consisting of one copy of the spacer and one repeat, complex with a Cas nuclease. The CRISPR/Cas complex is then directed to DNA sequences (protospacer) complementary to the crRNA spacer sequence, where this RNA-Cas protein complex silences the target DNA through enzymatic cleavage of both strands.

The native bacterial type II CRISPR system requires four molecular components for targeted cleavage of exogenous DNAs: a Cas endonuclease (e.g., Cas9), the house-keeping RNaseIII, CRISPR RNA (crRNA) and trans-acting CRISPR RNA (tracrRNA). The latter two components form a dsRNA complex and bind to Cas9 resulting in an RNA-guided DNA endonuclease complex. For targeted genome modifications in eukaryotes, this system was simplified to two components: the Cas9 endonuclease and a chimeric crRNA-tracrRNA, called guide-RNA (gRNA) or, alternatively, single-guide RNA (sgRNA). Experiments initially conducted in eukaryotic systems determined that the RNaseIII component was not necessary to achieve targeted DNA cleavage. The minimal two component system of Cas9 with the sgRNA, as the only unique component, enables this CRISPR system of targeted genome modification to be more cost effective and flexible than other targeting platforms such as meganucleases, Zn-finger nucleases, or TALE-nucleases which require protein engineering for modification at each targeted DNA site. Additionally, the ease of design and production of sgRNAs provides the CRISPR system with several advantages for application of targeted genome modification. For example, the CRISPR/Cas complex components (Cas endonuclease, sgRNA, and, optionally, exogenous DNA for integration into the genome) designed for one or more genomic target sites can be multiplexed in one transformation, or the introduction of the CRISPR/Cas complex components can be spatially and/or temporally separated.

In addition to the type II CRISPR, a new type V CRISPR has been discovered in recent years. To date, the experimentally tested type V CRISPR systems include the use of the following effector proteins which have been redesignated as Cas12a-e: Cas12a (also known as Cpf1; subtype V-A), Cas12b (also known as C2c1; subtype V-B), Cas12c (also known as C2c3; subtype V-C), Cas12d (also known as CasY; subtype V-D) and Cas12e (also known as CasX; subtype V-E), all of which are evolutionarily distinct from Cas9.

Thus, a construct comprising a sequence encoding a single guide RNA designed to target the KRN2 gene, wherein the expression of the construct in a plant together with the expression of a Cas-associated gene results in inhibited expression of the KRN2 gene is also encompassed in the scope of the present invention. The Cas-associated gene can be cloned into the same construct with the single guide RNA or into a separate construct for expression. The methods for delivery of said construct into a plant cell are known in the art.

The construct encoding a Cas-associated gene may comprise a promoter. In certain embodiments, the promoter is a constitutive promoter, a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the CRISPR system to only those cells in which DNA is inherited in subsequent generations. Therefore, a CRISPR-mediated genetic modification (i.e., chromosomal or episomal dsDNA cleavage) is limited only to cells that are involved in transmitting their genome from one generation to the next. This might be useful if broader expression of the CRISPR system were genotoxic or had other unwanted effects. Examples of such promoters include the promoters of genes encoding DNA ligases, recombinases, replicases, and so on. The present invention also provides transgenic plants with increased kernel row number or increased yield produced according to the method of the invention. The present invention also provides a commodity product made from the transgenic plant or plant parts thereof prepared according to the method of the invention. In one embodiment, the commodity is protein concentrate, protein isolate, cereal, starch, seeds, meal, flour, biomass or seed oil.

Further, after primary mapping of qKRN2, the inventors developed new molecular markers closely linked to KRN2 and the corresponding primers, which is useful in the screening of the kernel row number trait and paves the way for further fine mapping of qKRN2 and marker-assisted selection breeding, thus to expedite the breeding progress of high-yield maize. Accordingly, the present invention provides molecular markers and corresponding primers useful in identifying or assistantly identifying the kernel row number trait in maize, wherein said molecular markers are located from 16.37 Mb to 17.56 Mb on chromosome 2. In a preferable embodiment, the molecular markers are DNA fragments amplified by PCR using the maize genomic DNA as template with at least one pair of primers selected from SEQ ID NOs: 4-17. The present invention also provides a kit for identifying or assistantly identifying the kernel row number trait in maize, comprising at least one pair of primers corresponding to the molecular markers located from 16.37 Mb to 17.56 Mb on chromosome 2, preferably primers having sequences selected from SEQ ID NOs: 4-17. In yet another embodiment, the kit according to the present invention further comprises at least one selected from dNTP, DNA polymerase and PCR amplification buffer. Additionally, the present invention provide the use of said molecular markers and the corresponding primers as well as the kit in identifying or assistantly identifying the kernel row number trait in maize or in maize breeding.

FIGURES

FIG. 1: Comparison of KRN between B73 and MT-6. a and b. Ear performance of B73 and MT-6; c. KRN of B73 and MT-6.

Figure 2:
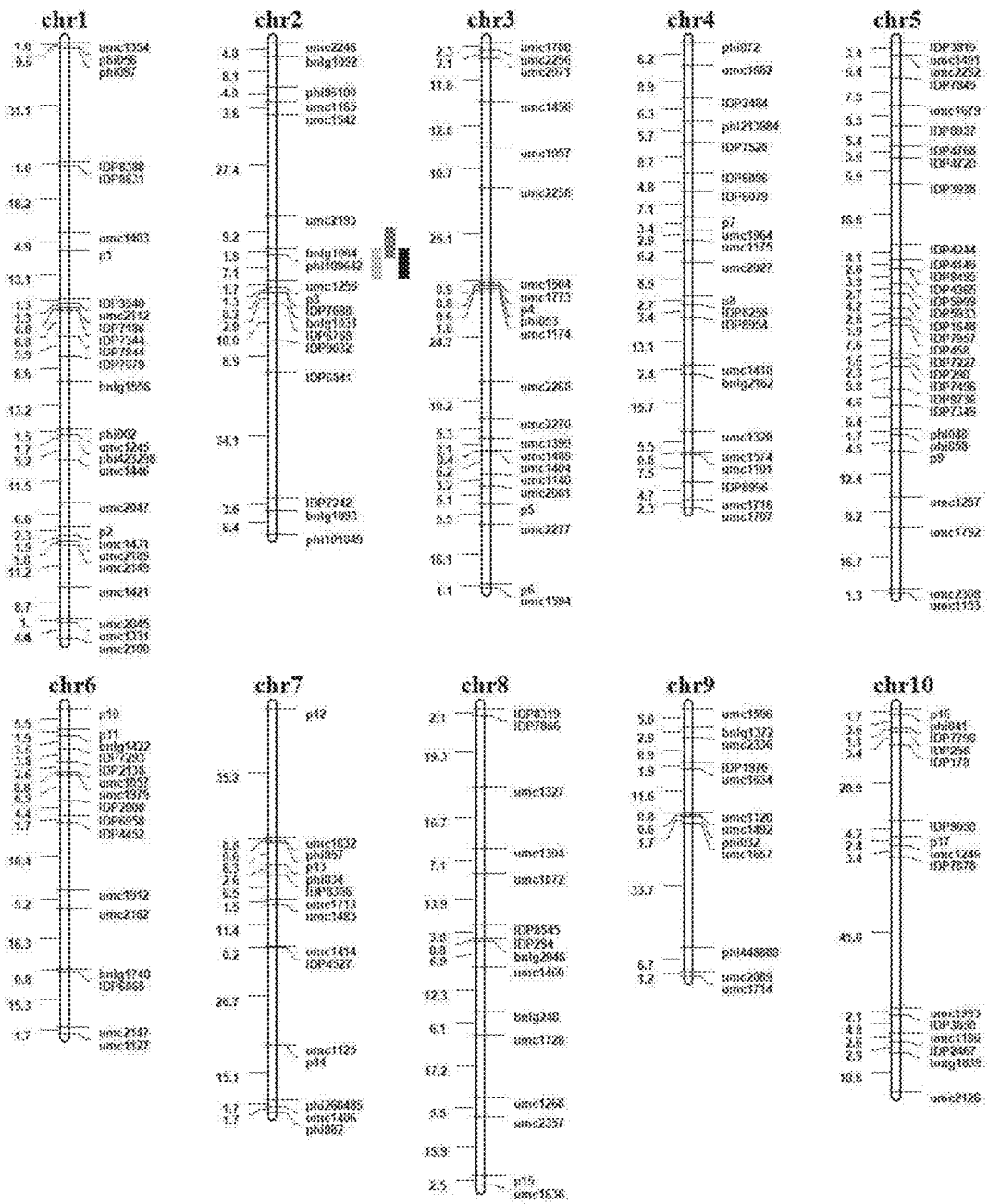

FIG. 2: Genetic map of the B73/MT-6 $F_2$ population, wherein the three boxes in light grey, dark grey and black represent the mapped QTL positions using data from three environments, Hainan, Beijing and Henan, respectively.

Figure 3:
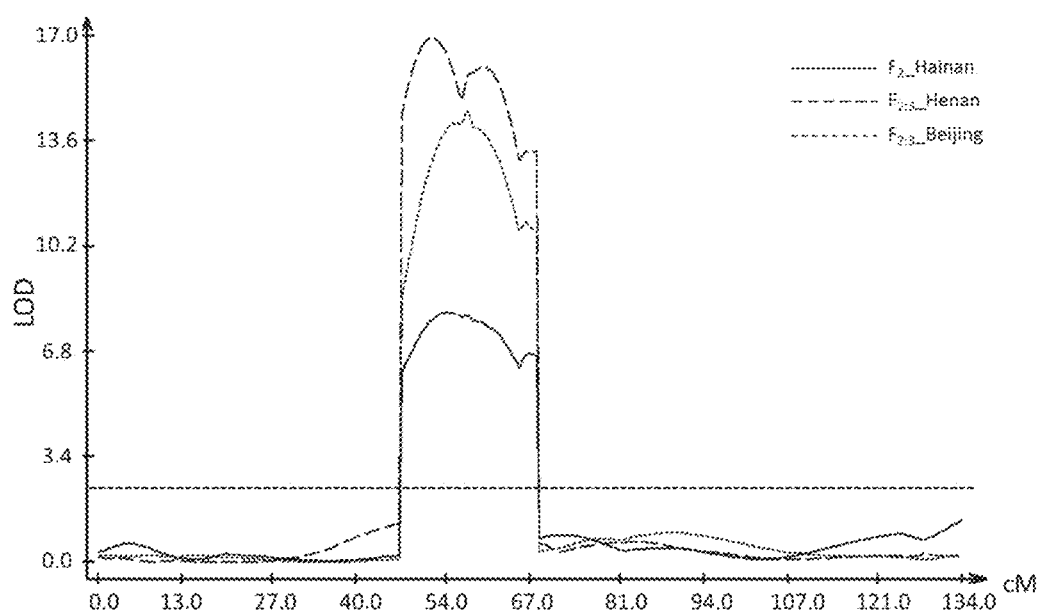

FIG. 3: LOD profile of the qKRN2.

Figure 4:
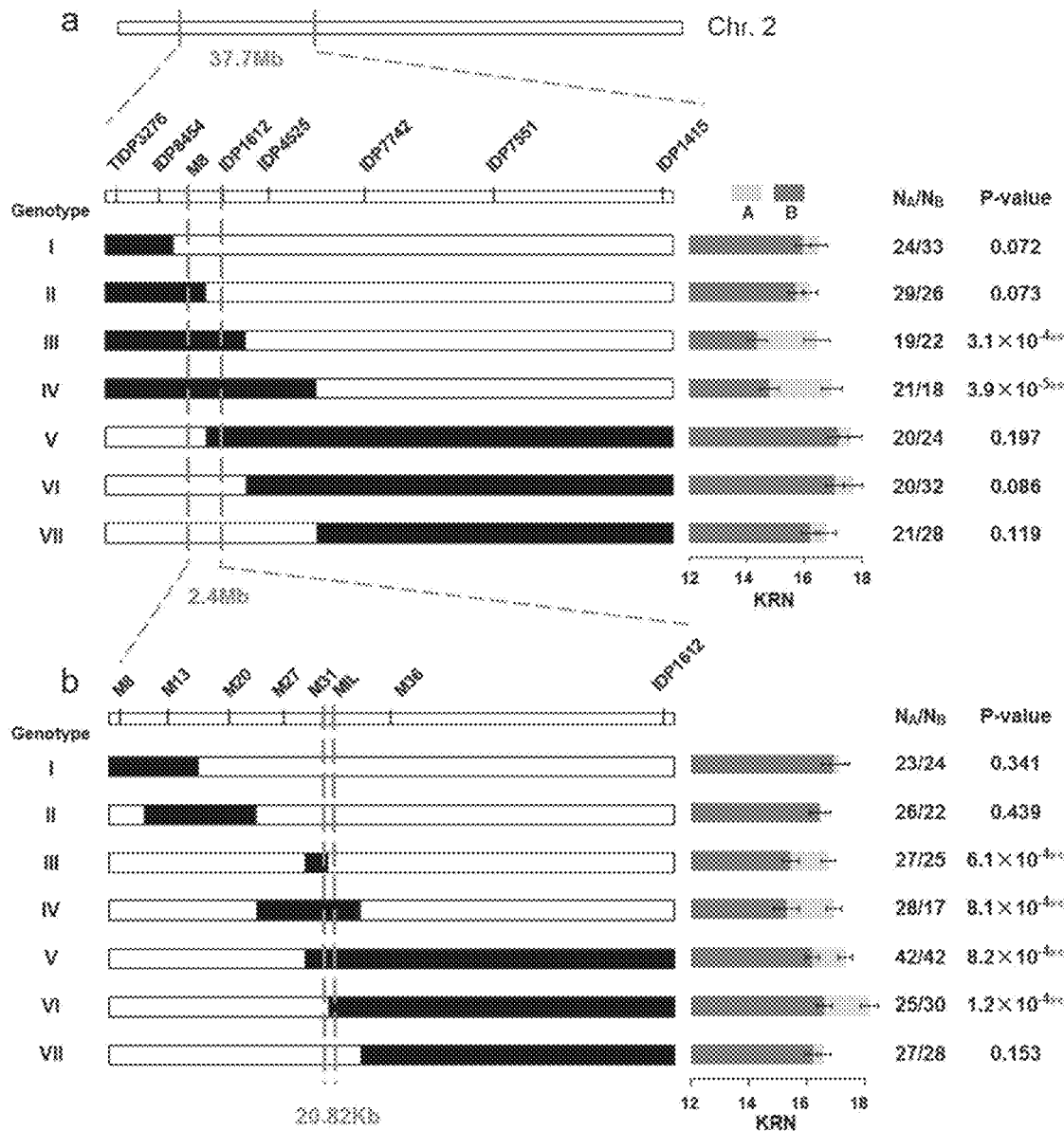

FIG. 4: a. primary fine mapping of qKRN2 using $BC_4F_2$ and $BC_5F_1$ recombinant plants, wherein qKRN2 was narrowed down to a region between markers M8 and IDP1612; b. further fine mapping of qKRN2 using $BC_4F_3$, $BC_5F_2$, $BC_5F_1$ and $BC_6F_1$ recombinant plants, wherein qKRN2 was narrowed down to a region between markers M31 and MIL. In FIGS. 4a and 4b, the genotype of different recombinant plants was shown in the left panel, wherein homozygous B73/B73 was shown in white box, heterozygous MT-6/B73 was shown in black box; the phenotype of homozygous progeny from selfed heterozygous recombinant plants was shown in the light panel, wherein homozygous B73/B73 was shown in light grey (A), homozygous MT-6/MT-6 was shown in dark grey (B). $N_A/N_B$ denotes the number of phenotype A/B. P-value represents the significance of difference between phenotype A and B in progeny of the same recombinant plant. ** denotes very significant difference statistically.

Figure 5:
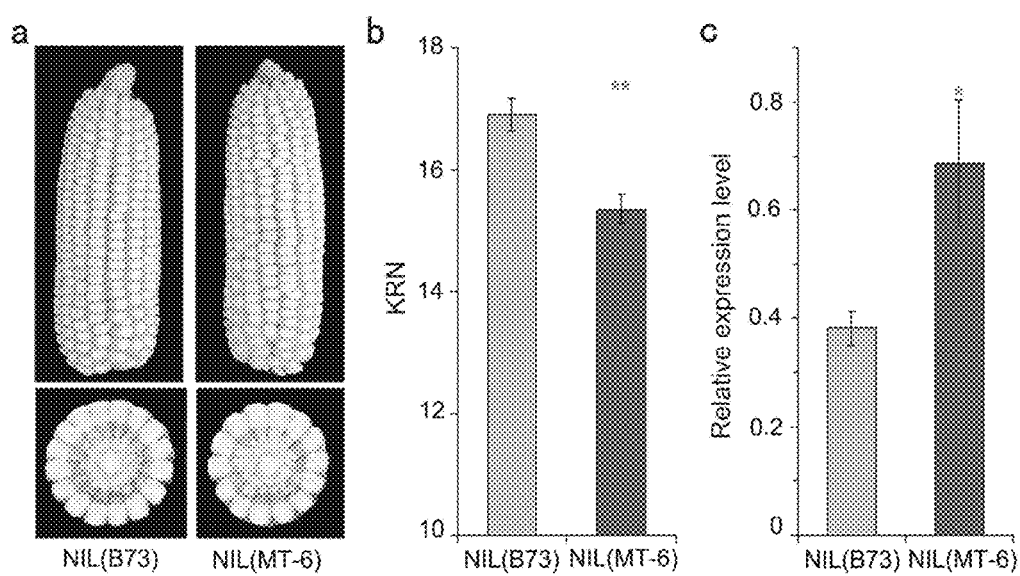

FIG. 5: a. Representative ears of near isogenic lines $NIL^{B73}$ and $NIL^{MT-6}$; b. statistical results of KRN of $NIL^{B73}$ and $NIL^{MT-6}$; c. expression levels of KRN2 in immature ear of $NIL^{B73}$ and $NIL^{MT-6}$. $NIL^{B73}$ is a near isogenic line in which the target segment is B73 allele; $NIL^{MT-6}$ is a near isogenic line in which the target segment is MT-6 allele. * denotes significant difference statistically; ** denotes very significant difference statistically.

Figure 6:
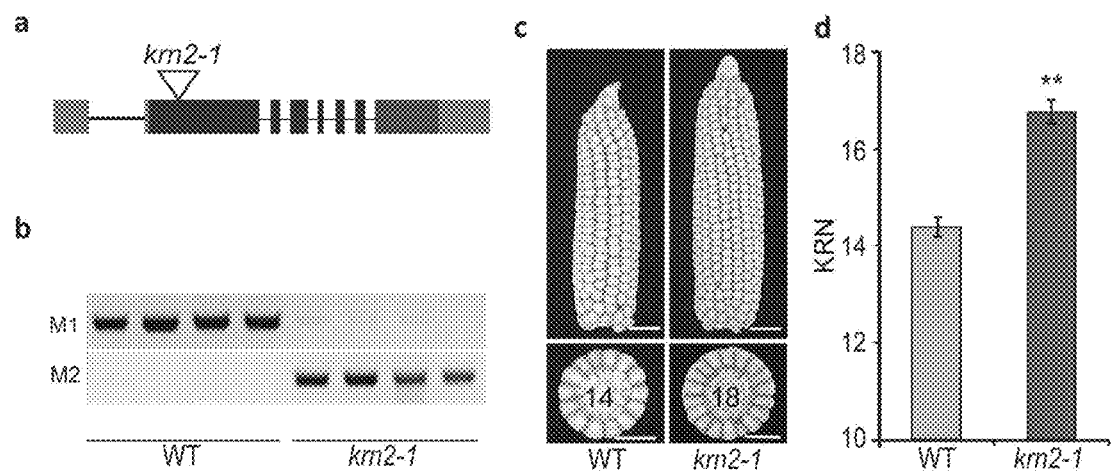

FIG. 6: a. gene structure of KRN2 and the insertion site of Mu transposon in mutant krn2-1; b. genotype of wild-type (WT) and mutant krn2-1, wherein M1 represents the PCR amplification result using specific upstream and downstream primers of the KRN2 gene, M2 represents the PCR amplification result using specific downstream primer of the KRN2 gene and primer TIR8-1 specific to the transposon; c. Representative ears of WT and krn2-1; d. statistical results of KRN of WT and krn2-1. ** denotes very significant difference statistically.

Figure 7:
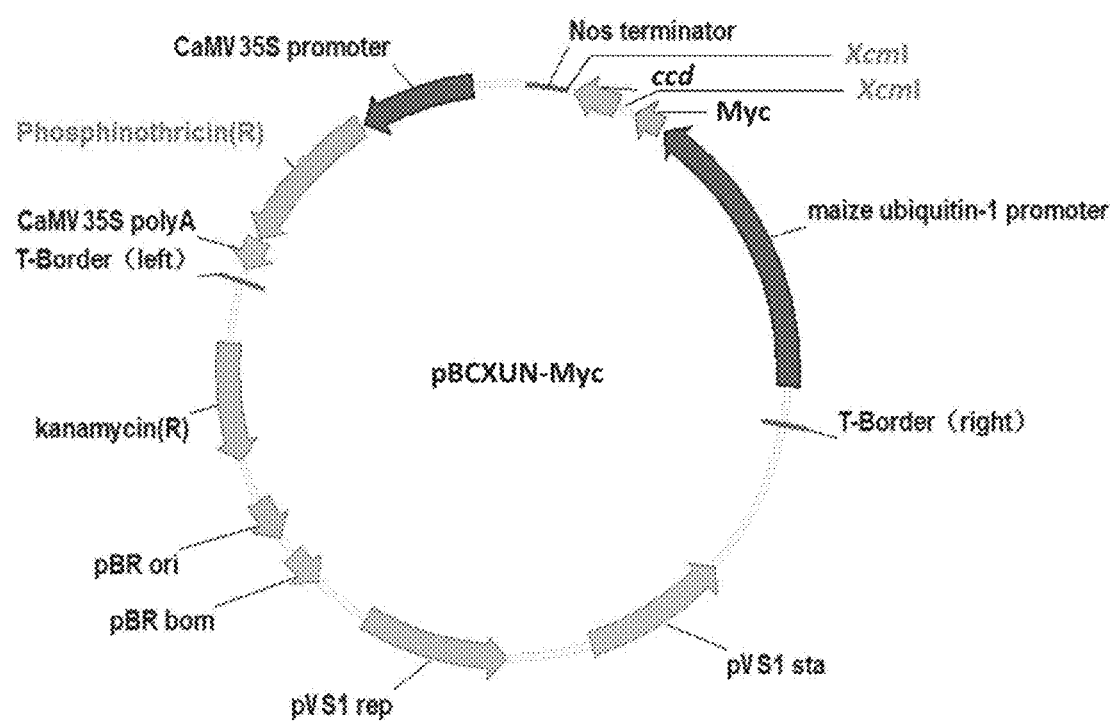

FIG. 7: Scheme of the vector pBCXUN-Myc used for overexpression.

Figure 8:
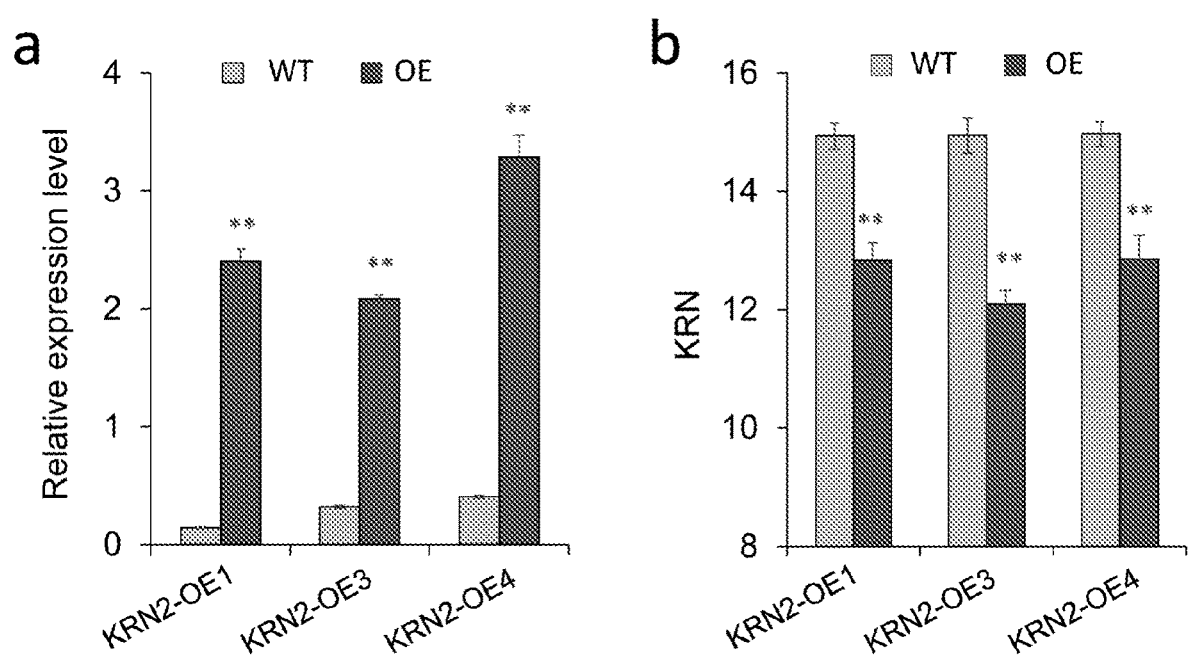

FIG. 8: Relative expression level of the KRN2 gene (a) and the statistical results of KRN (b) in KRN2-overexpressed maize lines (OE) and WT. ** denotes very significant difference statistically.

Figure 9:
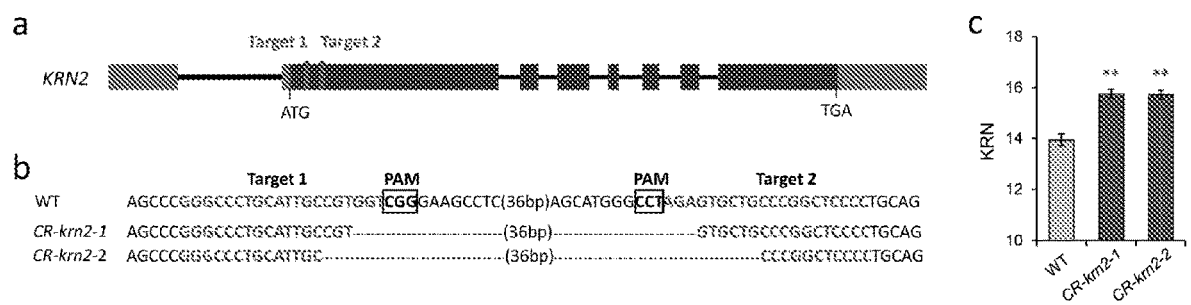

FIG. 9: Two target sites designed for the CRISPR/Cas9-mediated gene editing; b. sequencing results of new lines CR-krn2-1 and CR-krn2-2 produced by CRISPR/Cas9-mediated gene editing; c. the statistical results of KRN of CR-krn2-1 and CR-krn2-2. ** denotes very significant difference statistically.

Figure 10:
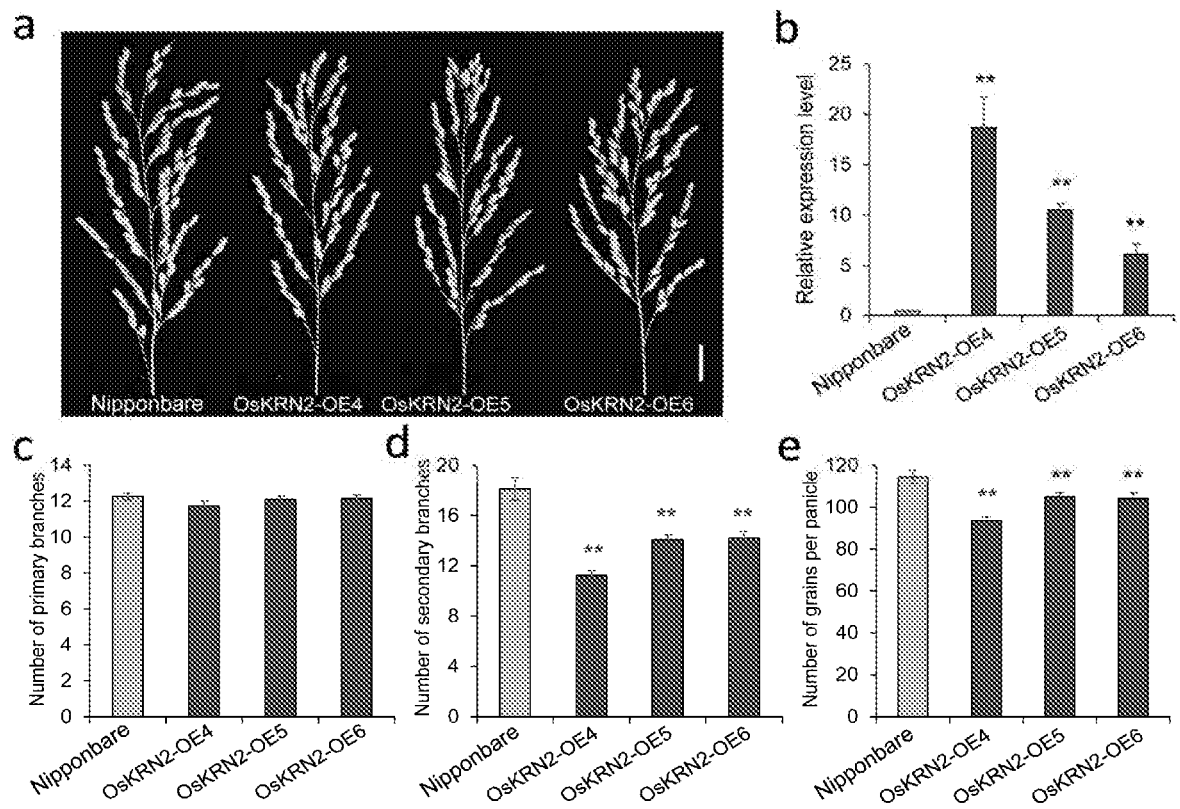

FIG. 10: Representative panicles of positive progeny plants of overexpressing transgenic lines (OE) in rice and Nipponbare (WT); b. relative expression levels of the OsKRN2 gene in the overexpressing transgenic lines (OE) in rice and Nipponbare (WT); c-e. the statistical results of primary branches (c), secondary branches (d) and grain number per panicle (e) in the overexpressing transgenic lines (OE) in rice and Nipponbare (WT). ** denotes very significant difference statistically.

Figure 11:
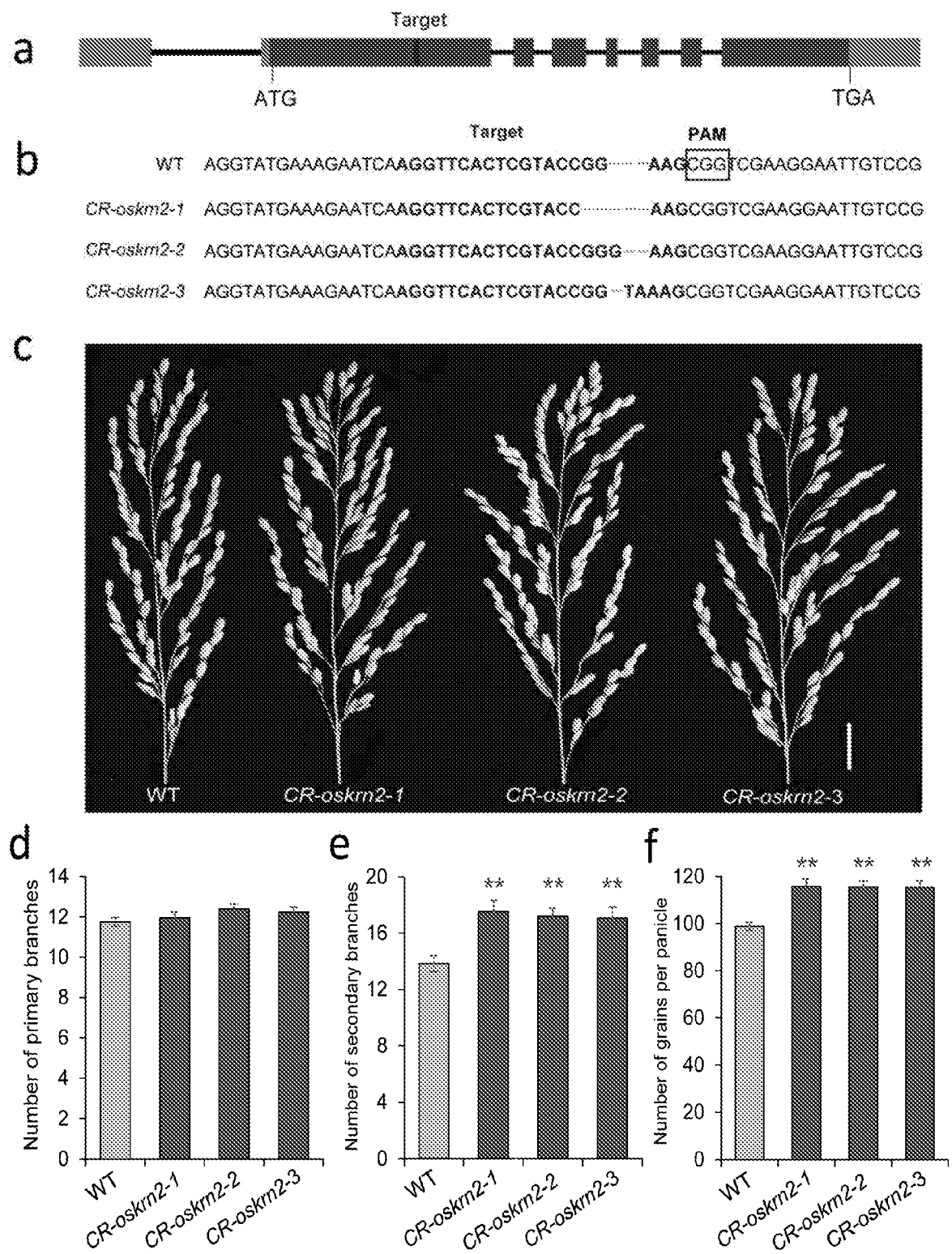

FIG. 11: a. A single target site designed for the CRISPR/Cas9-mediated gene editing; b. sequencing results of new lines CR-oskrn2-1, CR-oskrn2-2 and CR-oskrn2-3 produced by CRISPR/Cas9-mediated gene editing; c. representative rice panicles of three gene-edited lines and the corresponding WT; d-f. the statistical results of primary branches (d), secondary branches (e) and grain number per panicle (f) in the three gene-edited new lines and the corresponding WT. ** denotes very significant difference statistically.

Figure 12:
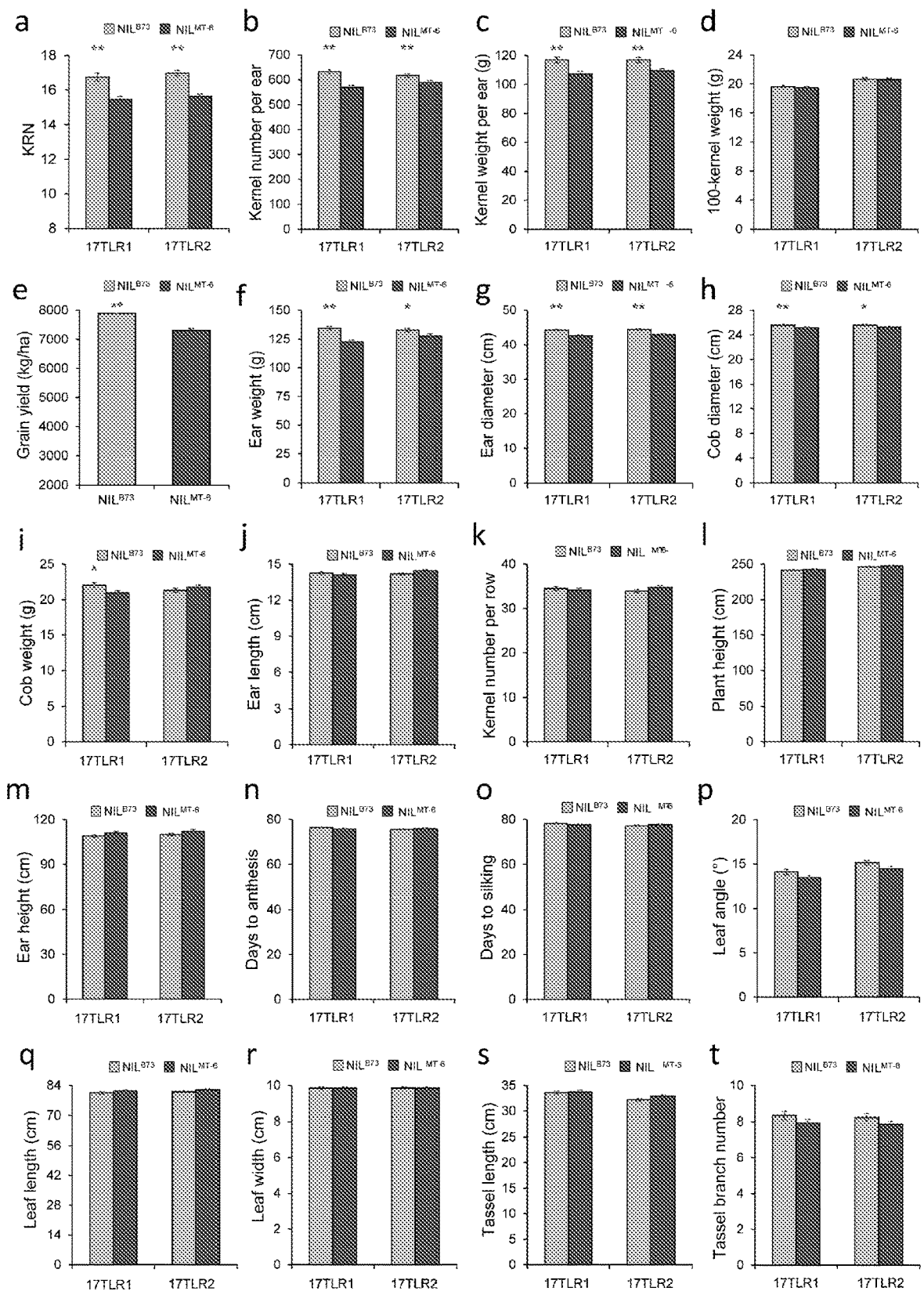

FIG. 12: the statistical results of multiple agricultural traits in near isogenic lines $NIL^{B73}$ and $NIL^{MT-6}$: KRN (a), kernel number per ear (b), kernel weight per ear (c), 100-kernel weight (d), grain yield (e), ear weight (f), ear diameter (g), cob diameter (h), cob weight (i), ear length (j), kernel number per row (k), plant height (l), ear height (m), days to anthesis (n), days to silking (o), leaf angle (p), leaf length (q), leaf width (r), tassel length (s) and tassel branch number (t). * denotes significant difference statistically; ** denotes very significant difference statistically.

EXAMPLES

The invention will be described in detail below with reference to the figures and the examples. It should be understood that the figures and examples of the present invention are intended to be illustrative only and do not limit the scope of the present invention in any way. The examples of the present application and the features in the examples may be combined with each other without contradiction.

Example 1: QTL Mapping for KRN in Maize

1. Development of a Maize Inbred Line MT-6

The maize inbred line Mo17 (187-2×C103, America), as the female parent, was crossed with the male parent teosinte X26-4 (Accession No. PI566686; Zea mays ssp. mexicana) to obtain $F_1$ generation, and progeny plants with fewer KRN was selected and selfed continuously, resulting in a material having a KRN of 6 which can be stably inherited. Said material is designated MT-6. FIG. 1 shows the comparison of KRN between B73 (BSSS, America) and MT-6.

2. Construction of the $F_2$ and $F_{2:3}$ Populations

The maize inbred line B73 was crossed with MT-6 to obtain $F_1$, one plant was selected and selfed to obtain 266 $F_2$ progeny plants, which forms the $F_2$ population. Meanwhile, each $F_2$ plant was selfed, resulting in 266 families which constitute the $F_{2:3}$ population.

3. Investigation of KRN in the $F_2$ and $F_{2:3}$ Populations

266 $F_2$ plants were grown in Hainan in 2010. Further, 266 $F_{2:3}$ families were grown in Beijing and Henan in 2011 using a randomized complete block design. Each $F_{2:3}$ family was grown in a single row (each row is 3 m, with 0.67 m distance between rows) at a density of 45,000 plants/hectare. Then, the KRN of each plant in the $F_2$ population and of 8 plants in each $F_{2:3}$ family (shown as an average value) was measured. The kernel row number per ear means the row number of grains in the ear. Results are shown in the following Table 1.

TABLE 1

KRN in the $F_2$ and $F_{2:3}$ populations

| Population/Condition | Average ± SD | Variation range |
|---|---|---|
| $F_2$/Hainan | 11.0 ± 1.5 | 8.0-16.0 |
| $F_{2:3}$/Beijing | 10.6 ± 1.3 | 8.0-14.7 |
| $F_{2:3}$/Henan | 10.1 ± 1.4 | 8.0-14.0 |

4. Screening of Polymorphic Markers

Polymorphic markers were selected in the whole genome from a public maize database (http://www.maziegdb.org). Primers were designed against each polymorphic marker, and were used for PCR amplification with the genomic DNA of B73 and MT-6 as template. The system and procedure for PCR amplification are shown in the following Table 2 and 3, respectively:

TABLE 2

PCR amplification system

| DNA (10 ng/μL) | 3 μL |
|---|---|
| 10 × buffer | 1.0 μL |
| dNTP (2.5 mM) | 0.8 μL |
| Forward primer (10 μM) | 0.3 μL |
| Reverse primer (10 μM) | 0.3 μL |
| Tag enzyme (2.5 U/μL) | 0.1 μL |
| ddH$_2$O | 4.5 μL |
| Total | 10 μL |

TABLE 3

PCR amplification procedure

| | Temperature | Time | Cycles |
|---|---|---|---|
| Step 1 | 95° C. | 5 min | 1 |
| Step 2 | 95° C. | 30 sec | 36 |
| | 56-62° C. | 30 sec | |
| | 72° C. | 60 sec | |
| Step 3 | 72° C. | 10 min | 1 |
| Step 4 | 15° C. | keep | |

The molecular markers polymorphic between B73 and MT-6 were selected to map QTL for KRN in the example. Finally, 192 polymorphic markers distributed on 10 chromosomes were obtained, as shown in FIG. 2.

5. Construction of a Linkage Map and Primary QTL Mapping for KRN

As shown in FIG. 2, the length of the genetic map of the B73/MT-6 $F_2$ population, constructed by 192 polymorphic markers is 1230.5 cM, and the average distance between markers is 6.4 cM. Together with the phenotypes (i.e., the observed KRN), QTL mapping was carried out for KRN using composite interval mapping (CIM) presented in Windows QTL Cartographer 2.5 software. The QTL controlling KRN was detected on chromosome 2, designated as qKRN2. As shown in FIG. 3, the LOD value of qKRN2 is always significantly greater than the threshold value of 3.4 in different generations or environments, indicating the presence of a QTL in this region (i.e., the detected result is true positive). Further as supported by the following Table 4, qKRN2 is located at around 55.0 cM in the genome, and the confidence interval is 18.2 cM (i.e., the genetic distance between the marker umc2193 and umc1259). This qKRN2 explains 9.4%-16.1% of the phenotypic variance, and is a major QTL controlling KRN in maize.

TABLE 4

Effects of qKRN2 in different generations or environments

| QTL | Flanked markers | Peak position of the max LOD | generation/ condition | Additive effect | Dominant effect | LOD value | contribution |
|---|---|---|---|---|---|---|---|
| qKRN2 | umc2193-umc1259 | 55.0 cM | $F_2$/Hainan | 0.76 | −0.02 | 8.1 | 9.4% |
| | | 51.0 cM | $F_{2:3}$/Beijing | 0.82 | 0.1 | 16.9 | 16.1% |
| | | 55.0 cM | $F_{2:3}$/Henan | 0.74 | 0.12 | 14.2 | 14.0% |

Example 2. Primary Fine Mapping of qKRN2

B73 was crossed with MT-6 to obtain $F_1$, which was back-crossed with B73 to obtain $BC_1F_1$. Plants with heterozygous alleles in the interval of QTL-qKRN2 were selected from the $BC_1F_1$ population using 8 markers between umc2193 and umc1259 (among them 7 markers are known: TIDP3276, IDP8454, IDP1612, IDP4525, IDP7742, IDP7551 and IDP1415; 1 marker is newly developed by the inventors: M8 between IDP8454 and IDP1612, the primer sequences of which are shown as SEQ ID NOs: 4 and 5), and continuously back-crossed with B73 until $BC_4F_1$ was obtained. The $BC_4F_1$ population was selfed, resulting in two homozygous lines with QTL-qKRN2 being B73 and MT-6 alleles, respectively (i.e., $NIL^{B73}$ and $NIL^{MT-6}$), which are designated as near isogenic lines.

Meanwhile, $BC_4F_1$ was selfed to obtain a $BC_4F_2$ population, and $BC_4F_1$ was back-crossed with B73 to obtain a $BC_5F_1$ population. Recombinant plants were screened using the above 8 molecular markers from around 10,000 $BC_4F_2$ and $BC_5F_1$ plants, in which the QTL region comprises multiple markers and one or more of markers are heterozygous. Recombinant plants in which the recombination site is between two different adjacent markers were selfed to produce new near isogenic lines.

The kernel row number of 30 $NIL^{B73}$ and $NIL^{MT-6}$ plants were investigated respectively, and Student's t tests were carried out the significant test. If the P value is greater than 0.05, there is no significant difference between KRN of near isogenic lines, and thus the different region of the near isogenic lines does not comprise the target qKRN2, if the P value is less than 0.05, there is significant difference between KRN of near isogenic lines, and thus the target qKRN2 falls within the different region of the near isogenic lines. The results of t test are shown in FIG. 4a. Accordingly, the target region was further narrowed down to around 2.4-Mb genomic interval between the markers M8 and IDP1612.

Example 3. Further Fine Mapping of qKRN2

1. Design of New Polymorphic Markers

Primers were designed against the genomic sequence between markers M8 and IDP1612 in B73 using the Primer5.0 software. PCR amplification was performed on the genomic DNA of B73 and MT-6 plants using the designed primers, and the amplified products were isolated using gel electrophoresis. Markers (InDel markers) resulting in amplified products polymorphic between B73 and MT-6 are used for further fine mapping of qKRN2 in the example. The InDel markers and the corresponding primer sequences used for further fine mapping in the example are shown in Table 5.

TABLE 5

InDel markers and primer sequences between M8 and IDP1612

| Name | position | Upstream primer | Downstream primer | Amplified product (B73) |
|---|---|---|---|---|
| M8 | 16.37 Mb | CACAAGACTACAAGGACGAGA (SEQ ID NO: 4) | GGCAGGAAGGAGGAAGAAGA (SEQ ID NO: 5) | 1260 bp |
| M13 | 16.58 Mb | CCGCAAATCTCCGCACAC (SEQ ID NO: 6) | TGATCCACCGCCAAAATACAG (SEQ ID NO: 7) | 1326 bp |
| M20 | 16.85 Mb | TAAGGGTGCGAATGGAAAG (SEQ ID NO: 8) | GGGGGACACGTCGTAGGT (SEQ ID NO: 9) | 845 bp |
| M27 | 17.09 Mb | GCTCGTTCCGTAGTGTAGTCTG (SEQ ID NO: 10) | CAGAACCACGACTATTTATCCG (SEQ ID NO: 11) | 736 bp |
| M31 | 17.276 Mb | ATGTCTCCCACTGCTGCTAC (SEQ ID NO: 12) | CCTCCGTGACCTCATCGTC (SEQ ID NO: 13) | 397 bp |
| MIL | 17.30 Mb | AGTTGATCGCTCGTCCTG (SEQ ID NO: 14) | TGTCAGGTGACCCATCCC (SEQ ID NO: 15) | 903 bp |
| M36 | 17.56 Mb | ACGGGCGACGAGAAGAAC (SEQ ID NO: 16) | CAGCATCAGACCCTCACTACC (SEQ ID NO: 17) | 973 bp |

New recombinant plants were screened from around 18,000 plants in the $BC_4F_3$, $BC_5F_2$, $BC_5F_1$ and $BC_6F_1$ populations using the above InDel markers. Specifically, the lines heterozygous in the target QTL region and with a significant KRN difference between near isogenic lines were selected from the $BC_4F_2$ and $BC_5F_1$ populations used for primary fine mapping. Said lines were selfed, resulted in $BC_4F_3$ and $BC_5F_2$ populations, and the selected $BC_5F_1$ lines were back-crossed with B73 to obtain $BC_6F_1$ population. The genotypes of the target QTL region were detected by the InDel markers as shown in Table 5. If the InDel markers exhibit a combination of B73 band and heterozygous band, it is defined as a recombinant plant. If said combination never appears in the $BC_4F_2$ and $BC_5F_1$ populations used for primary fine mapping, it is defined as a new recombinant plant.

The screened new recombinant plants were selfed, and t tests were performed for KRN of the progeny plants. If the P value is greater than 0.05, there is no significant difference between KRN of near isogenic lines, and thus the different region of the near isogenic lines does not comprise the target qKRN2, if the P value is less than 0.05, there is significant difference between KRN of near isogenic lines, and thus the target qKRN2 falls within the different region of the near isogenic lines. The results of t test are shown in FIG. 4b. Accordingly, the target region was further narrowed down to an around 20.82-Kb interval between the markers M31 and MIL.

Based on maize genome reference sequences, there is only one gene encoding a WD40 repeat protein between the markers M31 and MIL, and the inventors designated it as KRN2 gene in the present application. It is known that the WD40 repeat protein family plays multiple roles in the development of plants, including signaling, chromatin assembly, RNA processing and the like. However, its correlation with the kernel row number trait has not been reported yet.

The amino acid sequence of the protein encoded by KRN2 gene is shown in SEQ ID NO: 1. This protein consists of 696 amino acids, and comprises a protein domain, WD40 repeat sequence with unknown function.

The genomic sequence (including introns) of KRN2 gene is shown in SEQ ID NO: 2. This sequence consists of 7421 nucleotides, wherein nucleotides 368-3367 represent a promoter sequence.

The cDNA sequence of KRN2 gene is shown in SEQ ID NO: 3, which consists of 2853 nucleotides, and wherein nucleotides 310-2400 is the protein encoding sequence.

This KRN2 gene has not been cloned in maize yet, and there is no report regarding its homologous genes in other model plants such as *Arabidopsis* and rice. Thus, it is of significant importance to carry out a deep analysis on this gene.

Example 4. Analysis of KRN2 Effects

The kernel row number of 27 $NIL^{B73}$ plants and 25 $NIL^{MT-6}$ plants were investigated. It was observed that KRN of $NIL^{MT-6}$ is 1.3 rows fewer than that of $NIL^{B73}$ (P value<0.01, see FIG. 5 and Table 6). In terms of genotype, $NIL^{B73}$ and $NIL^{MT-6}$ have the same genetic background, with only difference lying in the region adjacent to the marker M31 (i.e., location of the KRN2 gene). In other words, the KRN difference between $NIL^{B73}$ and $NIL^{MT-6}$ is due to the KRN2 gene located in this region, a major QTL controlling the kernel row number trait.

TABLE 6

Analysis of KRN2 effects

| Markers | M8 | M27 | M31 | MIL | IDP 1612 | Average KRN ± SE | N | P value | effects |
|---|---|---|---|---|---|---|---|---|---|
| $NIL^{B73}$ | A | A | A | A | A | 16.71 ± 0.24 | 27 | $6.1 \times 10^{-4}$ | −1.3 |
| $NIL^{MT-6}$ | A | A | B | A | A | 15.43 ± 0.27 | 25 | | |

Notes: A denotes markers being the same as the parent B73, B denotes markers being the same as the parent MT-6.

The above statistical analysis results indicate that, the QTL identified in the present application, qKRN2, is a major QTL controlling the kernel row number trait.

The inventors also measured the expression level of KRN2 in immature ear of $NIL^{B73}$ and $NIL^{MT-6}$, and found that the KRN2 gene has a significant higher expression level in the immature ear of $NIL^{MT-6}$ than that in the immature ear of $NIL^{B73}$ (see FIG. 5c), indicating that the kernel row number trait is negatively regulated by the KRN2 gene. That is, the higher the expression level of KRN2 gene, the fewer the kernel row number.

Example 5: Verification of the Effects of KRN2 Gene Controlling Kernel Row Number in Maize A Mu transposon mutant of the KRN2 gene, krn2-1, was ordered from Maize Stock Center. The krn2-1 mutant has a Mu transposon inserted in the first exon of the KRN2 gene, specifically between the positions 682 and 683 of SEQ ID NO: 3, as shown in FIG. 6a. Wild type plants were identified using gene specific primers (upstream primer sequence: TAGGCTGTAGGATGGAGATG (SEQ ID NO: 18), and downstream primer sequence GACCTTGACCCTTTCAT-ACC (SEQ ID NO: 19)), and homozygous krn2-1 mutant plants were identified using the downstream primer sequence as shown in SEQ ID NO: 19 and a transposon specific primer TIR8-1: CGCCTCCAT-TTCGTCGAATCCCCTS (SEQ ID NO: 20). The results are shown in FIG. 6b. The transposon insertion in the KRN2 gene was confirmed in the krn2-1 mutant plants.

The phenotype of wild-type plants and krn2-1 mutants were investigated. As shown in FIGS. 6c and 6d, the wild type has an average KRN of 14.38, while the homozygous krn2-1 mutant has an average KRN of 16.76. Thus, the krn2-1 mutant has a significantly increased KRN compared to the wild-type, and the increased KRN is about 2.38.

Thus, it was confirmed that the KRN2 gene is capable of controlling the kernel row number trait in maize.

Example 6. Effects of KRN2 Gene Controlling KRN in Maize Verified by Overexpression Systems 1. Construction of a recombinant expression vector comprising a nucleic acid molecule encoding the KRN2 protein: a fragment of nucleotides 310-2400 of the cDNA as shown in SEQ ID NO: 3 was cloned into the overexpression vector pBCXUN-Myc (see FIG. 7) between two XcmI sites by enzyme digestion and ligation, and the promoter is Ubiquitin promoter. The recombinant expression vector was verified by sequencing.

2. The recombinant expression vector was transformed in the EHA105 Agrobacteria to obtain recombinant Agrobacteria comprising the recombinant expression vector, which was further used for transfection of embryo cells of maize lines, such that the nucleic acid molecule was integrated into the maize genome to obtain a recombinant cell. Methods for transformation of the expression vector and transfection of the Agrobacteria involved in this process as well as the used reagents are known to one skilled in the art.

3. The recombinant cell was cultured to obtain a transgenic maize seedling, from which at least one seed comprising the above nucleic acid molecule in its genome was collected.

Said seed was planted, the expression level of the KRN2 gene as well as the KRN phenotype were observed for the grown plants. FIG. 8 shows the expression level of the KRN2 gene (see FIG. 8a) as well as the KRN phenotype (see FIG. 8b) in three representative lines KRN2-OE1, KRN2-OE3 and KRN2-OE4. It was found that KRN of the three transgenic lines with overexpressed KRN2 gene have 2 rows fewer than the wild-type (P<0.01).

Example 7. Preparation of Maize Lines with Increased KRN by Gene Editing of the KRN2 Gene 1. Construction of CRISPR/Cas9 vectors each comprising a specific gRNA target in the KRN2 gene: two specific gRNA target sites in the KRN2 gene were selected (see FIG. 9a, gRNA-KRN2-1 sequence: GGCCCTGCAT-TGCCGTGGT (SEQ ID NO: 23), target site: nucleotides 3470-3488 of SEQ ID NO: 2; gRNA-KRN2-2 sequence: AGAGTGCTGCCCGGCTCCC (SEQ ID NO: 24), target site: nucleotides 3547-3565 of SEQ ID NO: 2), and two pairs of primers were designed accordingly. PCR amplification was performed using vector pCBC-MT1T2 as a template. PCR product was recovered and ligated into the pBUE411 vector using a digestion-ligation system comprising BsaI endonuclease and T4 ligase. A recombinant Cas9 vector was obtained and verified by PCR and sequencing. 2. The recombinant Cas9 vector was transformed in the EHA105 Agrobacteria to obtain recombinant Agrobacteria comprising the recombinant Cas9 vector, which was further used for transfection of embryo cells of maize lines, so as to obtain a recombinant cell.

3. The recombinant cell was cultured to obtain a transgenic maize seedling. The $T_0$ generation was sequenced and identified for the target sites. Maize new lines CR-krn2-1 and CR-krn2-2 having 64 bp and 73 bp deletion in the KRN2 gene were obtained respectively (see FIG. 9b). These two new lines have loss-of-function in the KRN2 gene.

Seeds of the new lines were planted, and the KRN phenotype was observed for the grown plants. Compared to the wild-type control, the KRN of the two new lines produced by gene editing increased around 1.8, which difference is statistically significant (see FIG. 9c).

Example 8. Application of InDel Markers of the Invention in Screening of the Breeding Material InDel markers of the invention as shown in Table 5 were used to detect the genotypes of the materials to be screened. Materials with the same bands as B73 were selected as excellent materials having increased KRN.

Specifically, the genotypes of various samples were detected by PCR using InDel markers of the invention as shown in Table 5, and statistical analysis was performed. Meanwhile, KRN of each sample was counted. Results are shown in Table 7.

TABLE 7

Analysis of KRN in different samples

| | B73 genotype | | MT-6 genotype | | | |
|---|---|---|---|---|---|---|
| Marker | Number of plants | Average KRN | Number of plants | Average KRN | KRN difference | P value |
| M8  | 33 | 17.03 | 54 | 15.3  | 1.73 | $6.06 \times 10^{-6}$ |
| M13 | 33 | 16.73 | 39 | 14.77 | 1.96 | $1.30 \times 10^{-7}$ |
| M20 | 31 | 18    | 27 | 16.52 | 1.48 | $8.91 \times 10^{-4}$ |
| M27 | 38 | 17.32 | 37 | 16    | 1.32 | $6.87 \times 10^{-5}$ |
| M31 | 26 | 16.77 | 33 | 15.09 | 1.68 | $7.89 \times 10^{-7}$ |
| MIL | 34 | 16.76 | 23 | 15.13 | 1.63 | $9.93 \times 10^{-5}$ |
| M36 | 29 | 17.1  | 37 | 15.83 | 1.27 | $4.21 \times 10^{-4}$ |

As shown in the above table, for marker M8, 33 plants having the B73 genotype exhibited an average KRN of 17.03, while 54 plants having the MT-6 genotype exhibited an average KRN of 15.3. That is, the KRN of maize materials having a low KRN2 expression level in the major QTL region is 1.73 more than that having a high KRN2 expression level, which difference is statistically significant. Thus, marker M8 can be used to effectively screen maize materials with more KRN, i.e., maize materials with low KRN2 expression level. Same results were observed for other markers M13, M20, M27, M31, MIL and M36.

Accordingly, the newly developed markers M8, M13, M20, M27, M31, MIL and M36 can be used to effectively screen maize with more KRN during the seedling stage, which saves the cost, improves the screening efficiency to select plants with more KRN in a faster manner, thus accelerating the breeding of high-yield maize.

Thus, the present invention developed new molecular markers within the major QTL qKRN2 region responsible for the kernel row number trait, increased the abundance of the molecular markers in the target region, and obtained linkage map of the molecular markers in the target region. Further, M8, M13, M20, M27, M31, MIL and M36 closely linked to the target QTL were obtained by further mapping analysis of the QTL, which molecular markers can be applied to screen the KRN trait of the maize material such that maize varieties or lines with more KRN can be selected effectively. The present application also provides marker information for studies related to the yield QTL in maize.

Example 9. Effects of KRN2 Homologous Gene in Arabidopsis

The inventors searched the Arabidopsis TIGR database using the amino acid sequence of maize KRN2 gene, and a protein sequence with Gene ID No. AT5G53500 was found to have the highest similarity with the KRN2 protein (a sequence identity of 40%). This homologous gene of KRN2 in Arabidopsis was designated as AtKRN2. CDS region of this AtKRN2 was ligated into the pCAMBIA 130 vector by digestion and ligation, so as to obtain an overexpression vector of AtKRN2 having a CaMV35S promoter. The recombinant expression vector was verified by sequencing.

Meanwhile, the AtKRN2 gene was edited by CRISPR/Cas9. Specifically, two specific gRNA target sites in the AtKRN2 gene were selected, and two pairs of primers were designed accordingly. PCR amplification was performed using vector pCBC-MT1T2 as a template. PCR product was recovered and ligated into the pHEE401e vector using a digestion-ligation system comprising BsaI endonuclease and T4 ligase. A recombinant Cas9 vector was obtained and verified by PCR and sequencing.

The above recombinant expression vector and recombinant Cas9 vector were transformed in the EHA105 Agrobacteria to obtain recombinant Agrobacteria comprising recombinant expression vector and and the recombinant Cas9 vector respectively, which recombinant Agrobacteria was further used for transfection of Arabidopsis (ecotype Columbia, $T_0$ generation) inflorescence, so as to obtain a recombinant cell. The $T_0$ generation was selfied to obtain $T_1$ seeds, and positive seedlings were identified subsequently.

The $T_1$ seeds were planted, and the AtKRN2 gene expression level as well as inflorescence phenotype in Arabidopsis are observed.

Example 10. Effects of KRN2 Homologous Gene in Rice

The inventors searched the NCBI database using the amino acid sequence of maize KRN2 gene, and a rice protein sequence with Gene ID No. OS04G0568400 (LOC_OS04G48010) was found to have the highest similarity with the KRN2 protein (a sequence identity of 74%). This homologous gene of KRN2 in rice was designated as OsKRN2 (SEQ ID NO: 21). CDS region of this OsKRN2 (SEQ ID NO: 22) was ligated into the pCUbi1390 vector by digestion and ligation, so as to obtain an overexpression vector of OsKRN2 in rice (Nipponbare background) deriven by a Ubiquitin promoter. The recombinant expression vector was verified by sequencing.

Meanwhile, the LOC_OS04G48010 gene was edited by CRISPR/Cas9. Specifically, a single specific gRNA target site in the OsKRN2 gene was selected (see FIG. 11a, gRNA-OsKRN2-1 sequence: aggttcactcgtaccggaag (SEQ ID NO: 25), target site: nucleotides 620-640 of SEQ ID NO: 21), and one pair of primers were designed accordingly. The primers were annealed to form a primer dimer, which was ligated to a CRISPR/Cas9 comprising the Cas9 gene using a digestion-ligation system comprising AarI endonuclease and T4 ligase. A recombinant Cas9 vector was obtained and verified by PCR and sequencing.

The above recombinant expression vector and recombinant Cas9 vector were transformed in the EHA105 Agrobacteria to obtain recombinant Agrobacteria comprising recombinant expression vector and the recombinant Cas9 vector respectively, which recombinant Agrobacteria was further used for transfection of Nipponbare callus, so as to obtain a recombinant cell. The positive seedlings were identified in the $T_0$ generation and $T_1$ seeds were harvested subsequently.

The $T_1$ seeds were planted, and the OsKRN2 gene expression level as well as grain number per panicle in rice were observed. Results show that all three overexpression lines had significantly increased OsKRN2 gene expression level (see FIG. 10b) and decreased grain number per panicle, primary and secondary branches (see FIG. 10c-e) compared to the wild-type control. Moreover, significantly increased grain number per panicle, primary and secondary branches were observed in three gene-edited lines CR-oskrn2-1, CR-oskrn2-2 and CR-oskrn2-3 (see FIG. 11).

Example 11. Potential Value of KRN2 Gene for Improving Maize Yield

Near isogenic lines NIL[B73] and NIL[MT-6] were grown in the same field environment (Tieling city, Liaoning Provence, 2017), and mulitiple agricultural traits were investigated for each plant, including days to anthesis, days to silking, ear height, plant height, leaf length, leaf width, leaf angle, tassel length, tassel branch number and the like. When the ears were matured and harvested, multiple traits of ears and kernels were investigated for well-grown ears, including ear weight, ear length, kernel number per row, kernel row number, ear diameter, kernel number per ear, kernel weight per ear, cob weight, cob diameter, 100-kernel weight, as well as grain yield. The experiment was repeated twice (i.e., 17TLR1 and 17TLR2).

The Student's t test were performed for multiple traits of near isogenic lines $NIL^{B73}$ and $NIL^{MT-6}$. The results show that in $NIL^{B73}$, KRN is significantly more than $NIL^{MT-6}$, while 100-kernel weight, ear length, and kernel number per row remains unchanged, resulting in significant higher kernel number per ear, kernel weight per ear, gain yield and ear weight than $NIL^{MT-6}$ (see FIGS. 12a-c and e-f). Besides, compared to $NIL^{MT-6}$, $NIL^{B73}$ also showed improved ear diameter, cob diameter and cob weight (see FIG. 12g-i). However, there was no significant difference in measured agricultural traits of plants (see FIG. 12l-t).

These results indicate that the KRN2 gene is able to increase kernel number per ear, kernel weight per ear and ear weight by increasing KRN, thus to improve maize yield, while not significantly affects other agricultural traits. This has important application value for the genetic improvement of high-yield new maize varieties.

---

What is claimed is:

1. A method of producing a transgenic maize plant having an increased kernel row number compared to a wild type maize plant, comprising obtaining a transgenic maize plant cell comprising a construct that inhibits expression of the KRN2 gene or the gene product thereof, and regenerating a transgenic maize plant comprising the construct from said transgenic maize plant cell.

2. The method according to claim 1, wherein the expression of the KRN2 gene or the gene product thereof is inhibited by RNA-mediated inhibition of the KRN2 gene.

3. The method according to claim 2, wherein the construct comprise a polynucleotide encoding a RNA molecule comprising a sequence that is at least 80% complementary to at least 19 continuous nucleotides of the KRN2 gene.

4. A transgenic plant produced by the method of claim 1.

5. A construct comprising a polynucleotide encoding an inhibitory RNA molecule comprising a sequence that is complementary to the the KRN2 gene, wherein the expression of the construct in a maize plant results in inhibited expression of the KRN2 gene.

6. The construct according to claim 5, wherein the RNA molecule is selected from the group consisting of an antisense RNA, MiRNA, and siRNA.

7. A transgenic maize plant, maize plant part, or maize plant cell comprising the construct of claim 5.

8. A commodity product made from the transgenic maize plant, maize plant part, or maize plant cell of claim 7, wherein the product comprises the construct comprising a polynucleotide encoding an inhibitory RNA molecule comprising a sequence that is complementary to the KRN2 gene.

9. The commodity product of claim 8, wherein the commodity product is protein concentrate, protein isolate, cereal, meal, flour, biomass.

10. The method according to claim 2, wherein the construct comprises a polynucleotide encoding a RNA molecule comprising a sequence that is at least 90% continuous nucleotides of the KRN2 gene.

11. The method according to claim 2, wherein the construct comprises a polynucleotide encoding a RNA molecule comprising a sequence that is 100% complementary to at least 19 continuous nucleotides of the KRN2 gene.

12. The transgenic maize plant of claim 7, wherein the transgenic maize plant has an increased yield as compared to a wild type maize plant not comprising the construct.

13. The method of claim 1, wherein the construct is introduced into the maize plant cell by a transformation method.

14. A transgenic maize plant part or plant cell of the transgenic maize plant of claim 4 or a progeny thereof, wherein the transgenic maize plant part or plant cell of the transgenic maize plant or the progeny thereof comprises the construct comprising a polynucleotide encoding an inhibitory RNA molecule comprising a sequence that is complementary to the KRN2 gene.

15. The maize transgenic plant part of claim 14, wherein the transgenic maize plant part is a transgenic maize seed.

16. The construct of claim 5, wherein the construct comprises a polynucleotide encoding a RNA molecule comprising a sequence that is at least 90% complementary to at least 19 continuous nucleotides of the KRN2 gene.

17. The construct of claim 5, wherein the construct comprises a polynucleotide encoding a RNA molecule comprising a sequence that is 100% complementary to at least 19 continuous nucleotides of the KRN2 gene.

18. The transgenic maize plant of claim 7, wherein the transgenic maize plant has an increased kernel row number relative to a wild type maize plant.

\* \* \* \* \*